United States Patent
Benkovic et al.

(10) Patent No.: US 9,309,508 B2
(45) Date of Patent: Apr. 12, 2016

(54) BORONIC AND BORINIC ACID COMPOUND AS INHIBITORS OF SULFENIC ACID-CONTAINING PROTEINS

(71) Applicants: Stephen Benkovic, State College, PA (US); Chunyu Liu, State College, PA (US); John W. Tomsho, Philadelphia, PA (US)

(72) Inventors: Stephen Benkovic, State College, PA (US); Chunyu Liu, State College, PA (US); John W. Tomsho, Philadelphia, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 14/576,613

(22) Filed: Dec. 19, 2014

(65) Prior Publication Data
US 2015/0140635 A1    May 21, 2015

Related U.S. Application Data

(62) Division of application No. 14/011,308, filed on Aug. 27, 2013, now Pat. No. 8,980,544.

(60) Provisional application No. 61/730,361, filed on Nov. 27, 2012.

(51) Int. Cl.
*C12N 9/99*    (2006.01)
*C12N 9/88*    (2006.01)

(52) U.S. Cl.
CPC .. *C12N 9/99* (2013.01); *C12N 9/88* (2013.01); *C12Y 402/01084* (2013.01)

(58) Field of Classification Search
CPC ............................................. C12Y 402/01084
See application file for complete search history.

(56) References Cited

U.S. PATENT DOCUMENTS

| | | | |
|---|---|---|---|
| 5,484,542 | A | 1/1996 | Cahoon et al. |
| 7,393,856 | B2 | 7/2008 | Bellinger-Kawahara et al. |
| 7,803,630 | B2 | 9/2010 | Poole et al. |
| 7,932,330 | B2 | 4/2011 | Oshima et al. |
| 8,115,026 | B2 | 2/2012 | Baker et al. |
| 8,168,614 | B2 | 5/2012 | Baker et al. |

OTHER PUBLICATIONS

Inglis et al. J. Med. Chem., 2009, 53:6097-6106.*
Adamczyk-Wopzniak et al., *J Organomet Chem*, 2009, 694:3533-3541.
PCT/US2013/057324 International Search Report and Written Opinion.
Adams et al., *Cancer Invest.*, 2004 22:304-311.
Albers et al., *J. Med. Chem.*, 2011, 54:4619-4626.
Anastasiou et al., *Science* 2011 344:1278-1283.
Asano et al., *ChemBioChem*, 2004 5: 483-490.
Baker et al., *Science* 2007 316:1759-1761.
Baker et al., *Chem. Soc. Rev.*, 2011 40:4279-4285.
Berge, *J. Pharm. Sci.* 1977 66(1)1-19.
Ellis et al., *J. Am. Chem. Soc.*, 2012 134:3631-3634.
Groziak, *Am. J. Therapeutics*, 2001 8:321-328.
Hashimoto et al., *J. Biol. Chem.* 2008 283:36617-36623.
Hill et al., *J. Mol. Cell. Cardiol.* (2012) 52:559-567.
Jacob et al., *Chem. Res. Toxicol.* 2012 25:588-604.
Kice et al., *J. Org. Chem.* 1989 54:4198-4203.
Leonard et al., *ACS Chem Biol*, 2009 4(9):783-799.
Mahajan et al., *J. Biol. Chem.* 2013 288:11611-11620.
Meng et al., *Mol. Cell*, 2002, 9:387-399.
Nishiyabu et al., *Chem. Commun.*, 2012 47:1106-1123.
Paulsen et al., *ACS Chem. Biol.*, 2010 5(1):47-62.
Paulsen et al., *Chem. Rev.* 2013 113:4633-4679.
Roos et al., *Free Radic. Biol. Med.* 2011 51:314-326.
Seo et al., *Proc. Natl. Acad. Sci. USA* 2009 106:16163-16168.
Svoboda et al., *Circ. Res.* 2012 111:842-853.
Winterbourn et al., *Free Radical Boi. Med.* 2008 45:549-561.
Zito et al., *Mol. Cell* 2012 48:39-51.
Liu et al., *J. Am. Chem. Soc.* 2013 135: 14544-14547.
Martinez et al., *J. Am. Chem. Soc.*, Just Accepted Manuscript, Published on the web Jan. 2, 2014.
Zervosen et al., *J. Am. Chem. Soc.*, 133:10839-10848 (2011).
Dzhekieva et al., *Biochemistry*, 49:6411-6419 (2010).

* cited by examiner

*Primary Examiner* — Bin Shen
(74) *Attorney, Agent, or Firm* — Husch Blackwell, LLP

(57) ABSTRACT

A boronic or borinic acid compound is used to inhibit the activity of a sulfenic acid-containing protein. Thus, a biologically-active sulfenic acid-containing protein is contacted with an activity-inhibiting effective amount of a boronic or borinic acid compound of Formula I or a salt, hydrate or solvate thereof, whose components are disclosed within, and that contact is maintained for a time sufficient to inhibit the biological activity of the protein.

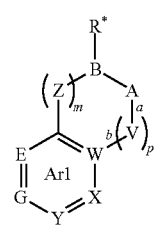

I

10 Claims, No Drawings

BORONIC AND BORINIC ACID COMPOUND AS INHIBITORS OF SULFENIC ACID-CONTAINING PROTEINS

CROSS-REFERENCE TO RELATED APPLICATIONS

This application is a division of application Ser. No. 14/011,308 filed on Aug. 27, 2013, that is now U.S. Pat. No. 8,980,544, and claims priority to U.S. application Ser. No. 61/730,361, filed on Nov. 27, 2012, whose disclosures are incorporated herein by reference.

TECHNICAL FIELD

The present invention contemplates a method of inhibiting the biologic activity of a biologically-active sulfenic acid-containing protein, and more particularly the inhibition of the biologic activity of a biologically-active sulfenic acid-containing protein such as an enzyme by contacting that protein with an activity-inhibiting effective amount of a boronic acid or borinic acid compound.

BACKGROUND ART

The formation of sulfenic acid groups in proteins has been recently recognized as a key event in many important biological processes. Sulfenic acids (Cys-SOH) arise from the oxidation of the thiol group of cysteine. Recent work has indicated that cellular oxidants (reactive oxygen species, ROS) are involved in cellular signaling and regulation. (See, Leonard et al., *ACS Chem Biol,* 2009 4(9):783-799 and references 1-3 therein).

A common reversible redox process of a protein cysteine is illustrated below. In one direction, oxidation of cysteine in the presence of ROS, such as hydrogen peroxide ($H_2O_2$), generates the corresponding sulfenic acid.

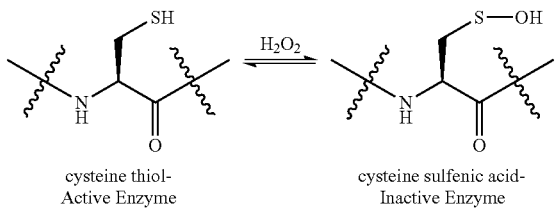 [SMILES: *N[C@@H](CS)C(*)=O ; "H2O2" ; *N[C@@H](CSO)C(*)=O]

cysteine thiol-
Active Enzyme cysteine sulfenic acid-
Inactive Enzyme

In some cases, such as with protein-tyrosine phosphatase 1B (PTP1B; EC 3.1.3.48), this oxidative modification converts the active enzyme (with a catalytic cysteine) to an inactive form containing a sulfenic acid, Cys-SOH (see, Meng et al., *Mol. Cell,* 2002, 9:387-399; Salmeen et al., *Nature,* 2003 423:769-773; and van Montfort et al., *Nature,* 2003 423:773-777 and references therein). Sulfenic acid formation in a protein contemplated by this invention leads to the biological activity that is inhibited by a contemplated compound as is discussed hereinafter.

A sulfinic acid generated by a reactive oxygen species such as hydrogen peroxide is often the intermediate to further modifications such as disulfide bond formation, S-glutathiolation, S-nitrosation, and sulfenyl amide formation [Paulsen et al., *Chem. Rev.* 2013 113:4633-4679; Jacob et al., *Chem. Res. Toxicol.* 2012 25:588-604; and Winterbourn et al., *Free Radical Bio. Med.* 2008 45:549-561]. The reversible nature of cysteine oxidation is analogous to phosphorylation, making them both well suited for regulatory posttransloational modifications. This also means that biological sulfenic acids can be a new class of potential pharmaceutical targets, especially given the growing implications of cysteine-derived sulfenic acids' role in health issues such as cancer, [Mahajan et al., *J. Biol. Chem.* 2013 288:11611-11620; Anastasiou et al., *Science* 2011 334:1278-1283; Seo et al., *Proc. Natl. Acad. Sci. USA* 2009 106:16163-16168] heart disease [Svoboda et al., *Circ. Res.* 2012 111:842-853], and scurvy [Zito et al., *Mol. Cell* 2012 48:39-51].

The articles cited below illustrate and highlight the diverse scope and prevalence of sulfenic acid groups in biologically active protein systems. Li et al., *J Mol Biol* 2005 346:1035-1046; Hill et al., *J Mol Cell Cardiol* 2012 52:559-567; Brigelius-Flohe' et al., *Anitoxid Redox Signal* 2011 15(8):2335-2381; Seo et al., *Proc Natl Adad Sci USA* 2009 106(38): 16163-16168; Paulsen et al., *Nature Chem Biol* 2012 8:57-64; Maccari et al., *J Med Chem* 2012 55:2-22; Roos et al., *Free Rad Bio Med* 2011 51:314-326; Jacob et al., *Chem Res Toxicol* 2012 25:588-604; Paulsen et al., *ACS Chem Biol* 2010 5(1):47-62; Wood et al., *Trends Biochem Sci* 2003 28(1):32-40; and Tonks, Nat Rev *Mol Cell Biol* 2006 7:833-846.

Among the known biologically-active proteins that contain/form sulfenic acids, most fall within three major classes: 1) phosphatases that are vital to the signaling pathway and the cell cycle; 2) peroxidases that play critical cellular antioxidant roles; and 3) the redox-modulated gene transcription factors that regulate protein expression level under different oxidative conditions. For example, Li et al., *J. Mol. Biol.* 2005 346:1035-1046 showed that *M. tuberculosis* encodes a 153-residue protein AhpE, which is a peroxidase of the 1-Cys peroxiredoxin (Prx) family, EC 1.11.1.15. The ahpC gene is widespread in microorganisms, and its gene product AhpC belongs to the nonheme peroxiredoxin (Prx) family, whose members are found in a wide range of biological systems, from bacteria to mammalian cells.

The importance of the Prxs, throughout living systems, is underlined by their extremely high abundance in both prokaryotic and mammalian cells. They are ubiquitous antioxidant enzymes that are expressed at high levels in cells. They are responsible for reducing a broad range of toxic peroxides and peroxinitrites (Tripathi et al., *Protoplasma,* 2009 235:3-15). All Prxs share a common reactive Cys residue in their N-terminal region, which is oxidized by peroxides to a cysteine sulfenic acid (Cys-SOH). The regeneration of the reduced form (back to Cys-SH) is necessary for the enzyme to regain its catalytic function. Depending on the presence or absence of other conserved cysteine residues in the sequence, Prx proteins can then be divided into 2-Cys and 1-Cys types. The 1-Cys Prx proteins are less well characterized with three dimensional structural reported for only one family member, human hORF6. Sequence alignment of AhpE with the human 1-Cys Prx, hORF6, showed that it is homologous with this protein also, but with lower sequence identity (24%), and that it lacks the C-terminal domain that mediates dimerization of hORF6.

The Hill et al., *J. Mol. Cell. Cardiol.* (2012) 52:559-567 review showed that the sulfenylated cysteine can react with glutathione (GSH) to form protein-mixed disulfides. A symmetrical set of reactions can also occur in which the thiolate of GSH is activated either by radical abstraction or sulfenic acid formation. Indeed, several proteins, such as hemoglobin, peroxiredoxins, the 20S proteasome, branched-chain aminotransferase, β-actin, inhibitor of nuclear factor κB kinase subunit β (IKK-β) and aldose reductase (AR), have been shown to be glutathiolated via a sulfenic acid intermediate. Thus, proteins can be glutathiolated as a result of activation of protein cysteine residues by sulfenylation.

Most thiols (SH-containing compounds) do not react at physiologically significant rates with hydroperoxides or other reactive species. Protein-bound cysteines are not particularly reactive unless they are embedded in a micro-architecture that facilitates cleavage of the hydroperoxy bond by polarization and proton shuttling as in the thiol peroxidases. Evolution has designed these proteins for highly efficient hydroperoxide reduction. Accordingly, they do not only deserve interest as hydroperoxide-detoxifying enzymes, but also as ideal sensors for a hydroperoxide compound (ROOH).

Yet several proteins, such as Prx and thioredoxin, contain a micro-architecture embedded cysteine that is in the thiolate form that readily reacts with $H_2O_2$ to form sulfenic acid (Cys-SOH); the sulfenylated residue can then facilitate glutathiolation reactions. For example, the sulfenic acid form of protein tyrosine phosphatase 1B (PTP1B; EC 3.1.3.48) is rapidly converted to a sulfenyl-amide (Cys-S—N—R), which prevents further oxidation to sulfinic and sulfonic acids and promotes glutathiolation and thiol recovery.

Sulfenic acids can also be stabilized non-covalently by interactions with surrounding residues. Glutathione reductase and NADH peroxidase form stabilized sulfenic acids that can favor thiolation reactions. Aldose reductase forms an apparently stable protein-sulfenic acid at Cys298 during ischemia that is glutathiolated enzymatically by GSTP upon reperfusion. Hence, a stabilized sulfenic acid can impart specificity to protein glutathiolation.

The Seo et al., *Proc Natl Adad Sci USA* 2009 106(38): 16163-16168 paper demonstrated that cancer cells are frequently under persistent oxidative stress due to oncogenic stimulation, increased metabolic activity, and mitochondrial malfunction. Elevated reactive oxygen species (ROS) generation in cancer cells serves as an endogenous source of DNA-damaging agents that promote genetic instability. Mounting evidence (see Roos et al., *Free Radic. Biol. Med.* 2011 51:314-326; Paulsen et al., *ACS Chem. Biol.*, 2010 5(1):47-62 and references therein) also supports a physiological role for ROS as second messengers in intracellular signaling cascades that control cell growth, proliferation, migration, and apoptosis.

In these pathways, stimulation of various cell surface receptors activates the NADPH oxidase complex to generate a burst of hydrogen peroxide ($H_2O_2$). $H_2O_2$ modulates signal transduction through chemoselective oxidation of cysteine residues in proteins, thereby altering their cellular function. In cancer cells, increased ROS can generate inappropriate proliferation signals and thus, contribute to tumor growth and other biological events that promote malignancy.

In a microarray screening study, Seo et al., *Proc Natl Adad Sci USA* 2009 106(38):16163-16168 reported that among the nine patient tumor tissue samples that examined, sulfenic acid abundance varied by up to seven-fold. In addition, six of seven individuals with transitional or squamous cell carcinoma exhibited a significant increase in the extent of sulfenic acid modifications, relative to matched normal tissue (P<0.005 by paired t test); adeno- and epidermoid bladder carcinomas samples were also associated with elevated levels of sulfenic acid (P<0.001 by paired t test). Although the number of paired samples on the array chip is too small to draw broad conclusions, these initial observations suggested to Seo et al. that elevated levels of sulfenic acid might be hallmark of bladder tumor tissues. Consistent with this hypothesis, lower total thiol groups have been reported in the blood plasma of patients with bladder cancer, as compared to healthy controls.

As indicated from the above-mentioned three categories of proteins, some of the proteins examined in the above papers are recognized for their enzymatic activity and have been given "EC" classification under the Enzyme commission report of 1961 and/or the Recommendations (1992) of the Nomenclature Committee of the International Union of Biochemistry and Molecular Biology, whereas others have not been so designated in the literature. Table A, below, provides names of exemplary proteins and their enzyme classification.

TABLE A

| Protein Name | Biological Activity | Enzyme Classification |
|---|---|---|
| Peroxiredoxin (Prxl); AhpE | Peroxidase | EC 1.11.1.15 |
| Protein tyrosine phosphatase 1B | Phosphatase; Cellular signaling | EC 3.1.3.48 |
| Aldose reductase | Reductase | EC 1.1.1.21 |
| Orp1 | Peroxidase; transcription regulator | — |
| GAPDH | Glucose metabolism and transcription regulator | EC 1.2.1.12 |
| Actin | Cytoskeleton component; Cell signaling | — |
| EGFR | Phosphorylase; Cellular signaling | — |
| Nitrile hydratase | Nitrile hydration | 4.2.1.84 |

Borinic acids, boronic acids, and their derivatives such as their esters, illustrated below with R's=hydrocarbyl, aryl, etc., are known to form dative bonds with biologically relevant alcohols such as ribose (see Baker et al., *Science*, 2007 316:1759-1761; Baker et. al., *J. Med. Chem.*, 2006 49:4447-4450; Zhu et al., *J. Am. Chem. Soc.*, 2006 128:1222-1232; Nishiyabu et al., *Chem. Commun.*, 2012 47:1106-1123; Ellis et al., *J. Am. Chem. Soc.*, 2012 134:3631-3634; and citations therein) and active site protein serines (see Adams et al., *Cancer Invest.*, 2004 22:304-311; Groll et al., *Structure*, 2006 14:451-456; Baldwin et al., *Bioorg. Med. Chem. Lett.*, 1991 1(1):9-12). Therefore, as inhibitors, boronic and borinic acids represent a class of compounds with attractive pharmaceutical applications (for a few examples see, Hall, in Boronic acids; Wiley-VCH: Weinheim, 2005 and citations therein; Groziak, *Am. J. Therapeutics*, 2001 8:321-328; Baker et al., *Chem. Soc. Rev.*, 2011 40:4279-4285; Priestley et al., *Bioorg. Med. Chem. Lett.*, 2002 12:3199-3202; Albers et al., *J. Med. Chem.*, 2011, 54:4619-4626; Baggio et al., *J. Am. Chem. Soc.*, 1997 119:8107-8108; Asano et al., *ChemBioChem*, 2004 5: 483-490; Baker et al., *Science* 2007 316:1759-1761; and Baker et. Al., *J. Med. Chem.*, 2006 49:4447-4450).

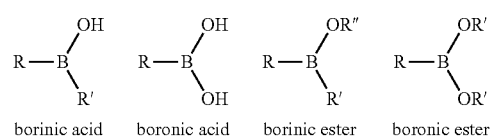

An underlying concept of this invention is that a contemplated boron-containing compound can form a dative bond (complex) specifically with the sulfenic acid form of a protein. The thiol form of the protein does not interact with the boron-containing compound. This complex formation permits specific trapping of the oxidized form of the protein. For example, in the case of PTP1B, this complex formation results in the trapping of the inactive form of the enzyme, thereby providing a novel mechanism of enzyme inactivation.

W is N, C, or $CR^4$;
X is N or $CR^5$;
Y is N or $CR^6$;

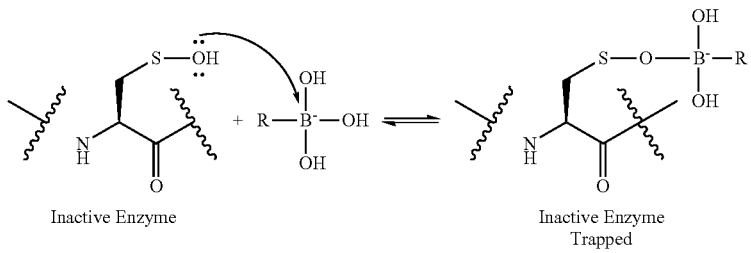

Inactive Enzyme          Inactive Enzyme Trapped

Nitrile hydratase provides an even more direct inhibition assay than does PTP. The catalytic activity of nitrile hydratase requires the presence of a catalytic cysteine-sulfenic acid (Cys-SOH). [Hashimoto et al., *J. Biol. Chem.* 2008 283: 36617-36623.] Thus, that enzyme provides a platform for a direct inhibition assay of catalytic activity. As shown hereinafter, the catalytic activity of nitrile hydratase is inhibited in the presence of boronic acids, thereby illustrating the utility of one aspect of the present invention.

Initial reviews of the scientific literature have failed to find any reports of borinic acid and/or boronic acid or their esters, salts, hydrates, or solvates being used for the targeting of protein sulfenic acids. Currently, it is believed that there are no reported therapeutics that specifically targeting the sulfenic acid protein modification.

BRIEF SUMMARY OF THE INVENTION

The present invention contemplates the inhibition of the activity of a sulfenic acid-containing protein using a boronic or borinic acid compound (derivative). More specifically, the present invention contemplates contacting a biologically-active sulfenic acid-containing protein with an activity-inhibiting effective amount of a boronic or borinic acid compound of Formula I or a salt, hydrate, or solvate thereof, and maintaining that contact for a time sufficient to inhibit the activity of that protein. A contemplated compound of Formula I is illustrated hereinbelow.

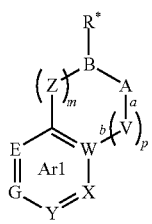

I wherein
A is oxygen (O) when p is 1 and bond a and bond b are present, or $R^7$ or $OR^7$ when bond a and bond b are absent and p is 0;
B is boron;
V is $CH_2$ when p is 1 and bonds a and b are present, and V is absent when p is 0 and bonds a and b are absent;
E is N, or $CR^2$;
G is N, or $CR^3$;

Z=O (oxygen) or $(CH_2)_nC(=O)O$, where n=0, 1 or 2, and m=0 or 1 such that Z is absent when m=0 and B is bonded directly to the aromatic or heteroaromatic ring, Ar1;
p=0 or 1, with the proviso that when p is 1, W is C, bonds a and b are present and m is 0, and when p is zero (0), all three of V, bond a and bond b are absent and W is N or $CR^4$;
m=is 0 or 1; m is 0 when p is 1, and m is 1 when p is 0 or 1, with the proviso that when m=1 at least one of A and R* is other than $OR^7$ and $OR^1$, respectively;
R* is $R^1$ or $OR^1$;
$R^1$ and $R^7$ are selected independently from the group consisting of hydrido (hydrogen; H), optionally substituted $C_1$-$C_8$ hydrocarbyl, optionally substituted aryl, ar$C_1$-$C_8$ hydrocarbyl, and optionally substituted heteroaryl, in which the optional substituents are $C_1$-$C_8$ hydrocarbyl, aryl, ar$C_1$-$C_8$ hydrocarbyl, heteroaryl, heteroar$C_1$-$C_8$ hydrocarbyl, heterocyclyl, cyclohydrocarbyloxy, heterocyclyloxy, —C(O)-aryl, hydrocarbyloxy, aryloxy, heteroaryloxy, —OC(O)—($C_1$-$C_8$ hydrocarbyl), —OCH$_2$CH$_2$OH, —O(CH$_2$)$_3$CO$_2$H, 2-(morpholino) ethoxy, —(CH$_2$)$_k$OH (where k=1, 2 or 3), —CH$_2$NH$_2$, —CH$_2$NH($C_1$-$C_8$ hydrocarbyl), —CH$_2$N($C_1$-$C_8$ hydrocarbyl)$_2$, halogen, formyl (—CHO), thioformyl (—CHS), —CH=NOH, —CO$_2$H, thiocarboxyl (—CSOH), sulfonyl (—HSO$_2$), $C_1$-$C_8$ hydrocarbylsulfonyl, arylsulfonyl, heteroarylsulfonyl, $C_1$-$C_8$ hydrocarbylsulfinyl, arylsulfinyl, heteroarylsulfinyl, —CO$_2$($C_1$-$C_8$ hydrocarbyl), —CONH$_2$, —CONH($C_1$-$C_8$ hydrocarbyl), —CON($C_1$-$C_8$ hydrocarbyl)$_2$, —OH, —SH, —S—($C_1$-$C_8$ hydrocarbyl), —S-aryl, —SO$_2$($C_1$-$C_8$ hydrocarbyl), —SO$_2$N($C_1$-$C_8$ hydrocarbyl)$_2$, $C_1$-$C_8$ hydrocarbylsulfonylamino (—SO$_2$NH $C_1$-$C_8$ hydrocarbyl), aryl sulfonylamino, —SO$_2$NH$_2$, —SO$_3$H, —SCF$_3$, —CN, —CHF$_2$, —CF$_3$, —NO$_2$, amino (—NH$_2$), —NH ($C_1$-$C_8$ hydrocarbyl, —N($C_1$-$C_8$ hydrocarbyl)$_2$, arylamino, diarylamino, —NHSO$_2$($C_1$-$C_8$ hydrocarbyl), —CONH($C_1$-$C_8$ hydrocarbyl), and —CON($C_1$-$C_8$ hydrocarbyl)$_2$.
$R^2$, $R^3$, $R^4$, $R^5$ and $R^6$ are independently selected from the group consisting of hydrogen (hydrido; H), $C_1$-$C_8$ hydrocarbyl, aryl, arC1-C8 hydrocarbyl, heteroaryl, heteroarC1-C8 hydrocarbyl, heterocyclyl, cyclohydrocarbyloxy, heterocyclyloxy, —C(O)-aryl, alkoxy, aryloxy, heteroaryloxy, —OC(O)-hydrocarbyl, —OCH$_2$CH$_2$OH, —O(CH$_2$)$_3$CO$_2$H, 2-(morpholino) ethoxy, —(CH$_2$)$_k$OH (where k=1, 2 or 3), —CH$_2$NH$_2$, —CH$_2$NH($C_1$-$C_8$ hydrocarbyl), —CH$_2$N($C_1$-$C_8$ hydrocarbyl)$_2$, halogen, formyl (—CHO), thioformyl (—CHS), —CH=NOH, —CO$_2$H, thiocarboxyl (—CSOH), sulfonyl (—HSO$_2$), C$_1$-C$_8$ hydrocarbylsulfonyl, arylsulfonyl, heteroarylsulfonyl, hydrocarbylsulfinyl, arylsulfinyl, heteroarylsulfinyl, —CO$_2$(C$_1$-C$_8$ hydrocarbyl), —CONH$_2$, —CONH(C$_1$-C$_8$ hydrocarbyl), —CON(C$_1$-C$_8$ hydrocarbyl)$_2$, —OH, —SH, —S—(C$_1$-C$_8$)hydrocarbyl, —S-aryl, —SO$_2$(C$_1$-C$_8$ hydrocarbyl), —SO$_2$N(C$_1$-C$_8$ hydrocarbyl)$_2$, C$_1$-C$_8$ hydrocarbyl sulfonylamino (—SO$_2$NH C$_1$-C$_8$ hydrocarbyl), aryl sulfonylamino, —SO$_2$NH$_2$, —SO$_3$H, —SCF$_3$, —CN, —CHF$_2$, —CF$_3$, —NO$_2$, amino (—NH$_2$), —NH (C$_1$-C$_8$ hydrocarbyl), —N(C$_1$-C$_8$ hydrocarbyl)$_2$, arylamino, diarylamino, —NHSO$_2$(C$_1$-C$_8$ hydrocarbyl), —C(O)NH(C$_1$-C$_8$ hydrocarbyl), and —C(O)N(C$_1$-C$_8$ hydrocarbyl)$_2$. The C$_1$-C$_8$ hydrocarbyl, aryl, arC$_1$-C$_8$ hydrocarbyl, heteroaryl, heteroarC$_1$-C$_8$ hydrocarbyl, cyclohydrocarbyl and heterocyclic groups in each of the R$^2$, R$^3$, R$^4$, R$^5$ and R$^6$ (R$^{2-6}$) substituents are themselves optionally substituted.

Alternatively, one or more adjacent pairs of R$^2$, R$^3$, R$^4$, R$^5$ and R$^6$ (such as R$^2$ and R$^3$, or R$^3$ and R$^4$, R$^4$ and R$^5$, or R$^5$ and R$^6$) together with the atoms to which they are bonded form an optionally substituted mono- or bicyclic aromatic ring or heteroaromatic ring Ar2.

A pharmaceutical composition containing a compound of Formula I dissolved or dispersed in a physiologically acceptable diluent or carrier is also contemplated. One or more compounds of Formula I can be present and a biological activity-inhibiting effective amount of such a compound need not be present in a given composition, but can be achieved through multiple contacting steps.

DEFINITIONS

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed to be subsumed within the aliphatic groups. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups, substituents, moieties or radicals, as discussed hereinafter. An arylhydrocarbyl substituent group such as benzyl is deemed an aromatic group as being an aromatic ring bonded to a hydrocarbyl group that is CH$_2$. A substituent group containing both an aliphatic ring and an aromatic ring portion such as tetralin (tetrahydronaphthalene) that is linked directly through the aliphatic portion is deemed a non-aromatic, hydrocarbyl group. On the other hand, a similar group bonded directly via the aromatic portion, is deemed to be a substituted aromatic group.

Exemplary hydrocarbyl groups contain a chain of 1 to about 8 carbon atoms, and more preferably 1 to 6 carbon atoms, and more preferably still 1 to about 4 carbon atoms. Examples of hydrocarbyl radicals include methyl, ethyl, n-propyl, isopropyl, n-butyl, isobutyl, sec-butyl, tert-butyl, pentyl, iso-amyl, hexyl, octyl, decyl, dodecyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

An alkyl group is a preferred hydrocarbyl group. As a consequence, a generalized, but more preferred substituent can be recited by replacing the descriptor "hydrocarbyl" with "alkyl" in any of the substituent groups enumerated herein. Where a specific aliphatic hydrocarbyl substituent group is intended, that group is recited; i.e., C$_1$-C$_4$ alkyl, methyl or dodecenyl.

A contemplated cyclohydrocarbyl substituent ring contains 3 to 8 carbon atoms. A preferred cyclohydrocarbyl substituent is a cycloalkyl group that contains 3 to 8 carbon atoms. The term "cycloalkylalkyl" means an alkyl radical as defined above that is substituted by a cycloalkyl radical containing 3 to about 8, preferably 3 to about 6, carbon atoms. Examples of such cycloalkyl radicals include cyclopropyl, cyclobutyl, cyclopentyl, cyclohexyl and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups. On the other hand, a hydrocarbyl group containing a —C(O)— functionality is referred to as a hydrocarboyl (acyl) and that containing a —C(O)O— is a hydrocarboyloxy group inasmuch as there is no ambiguity. Exemplary hydrocarboyl and hydrocarboyloxy groups include acyl and acyloxy groups, respectively, such as formyl, acetyl, propionyl, butyryl, valeryl, 4-methylvaleryl, and acetoxy, acryloyl and acryloyloxy.

A "carboxyl" substituent is a —C(O)OH group. A C$_1$-C$_8$ hydrocarbyl carboxylate is a C$_1$-C$_8$ hydrocarbyl ester of a carboxyl group. A carboxamide is a —C(O)NH$_2$ group or a similar group where one or both of the hydrogens of the depicted nitrogen is replaced by a hydrocarbyl group. Similarly, a sulfonamide is a —S(O)$_2$NH$_2$, or a similar group where one or both of the hydrogens of the depicted nitrogen is replaced by a hydrocarbyl group.

As a skilled worker will understand, a substituent that cannot exist such as a C$_1$ alkenyl or alkynyl group is not intended to be encompassed by the word "hydrocarbyl", although such substituents with two or more carbon atoms are intended.

The term "thiol" or "sulfhydryl", alone or in combination, means a —SH group. The term "thio" or "thia", alone or in combination, means a thioether group; i.e., an ether group wherein the ether oxygen is replaced by a sulfur atom.

The term "amino", alone or in combination, means an amine or —NH$_2$ group whereas the term mono-substituted amino, alone or in combination, means a substituted amine —N(H)(substituent) group wherein one hydrogen atom is replaced with a substituent, and disubstituted amine means a —N(substituent)$_2$ wherein two hydrogen atoms of the amino group are replaced with independently selected substituent groups.

Amines, amino groups and amides are compounds that can be designated as primary)(I°), secondary (II°) or tertiary (III°) or unsubstituted, mono-substituted or N,N-disubstituted depending on the degree of substitution of the amino nitrogen. Quaternary amine) (ammonium) (IV°) means a nitrogen with four substituents [—N$^+$ (substituent)$_4$] that is positively charged and accompanied by a counter ion, whereas N-oxide means one substituent is oxygen and the group is represented as [—N$^+$ (substituent)$_3$-O$^-$]; i.e., the charges are internally compensated.

The term "cyano", alone or in combination, means a —C-triple bond-N (—C≡N) group. The term "azido", alone or in combination, means a —N-triple bond-N (—N≡N) group. The term "hydroxyl", alone or in combination, means a —OH group. The term "nitro", alone or in combination, means a —NO$_2$ group.

The term "sulfonyl", alone or in combination, means a —SO$_2$— group wherein the depicted remaining two bonds (valences) can be independently substituted. The term "sulfoxido", alone or in combination, means a —SO— group wherein the remaining two bonds (valences) can be independently substituted.

The term "sulfone", alone or in combination, means a —SO$_2$— group wherein the depicted remaining two bonds (valences) can be independently substituted. The term "sulfenamide", alone or in combination, means a —SON= group wherein the remaining three depicted bonds (valences) can be independently substituted. The term "sulfide", alone or in combination, means a —S— group wherein the remaining two bonds (valences) can be independently substituted.

The term "aryl", alone or in combination, means an aromatic ring-containing moiety or a fused ring system containing two or three rings that have all carbon atoms in the ring, such as phenyl, naphthyl, indenyl or other aromatic hydrocarbon radical as recited hereinafter that optionally carries one or more substituents selected from C$_1$-C$_8$ hydrocarbyl, C$_1$-C$_8$ hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means a hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O— arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

A heterocyclic (heterocyclo) or heterocyclo portion of a heterocyclocarbonyl, heterocyclooxy-carbonyl, heterocycloalkoxycarbonyl, or heterocycloalkyl group or the like is a saturated or partially unsaturated 5- or 6-membered monocyclic substituent that contains one or more hetero atoms selected from nitrogen, oxygen and sulphur. Such a moiety can be optionally substituted on one or more ring carbon atoms by a preferred substituent selected from the group consisting of halogen, C$_1$-C$_8$ hydrocarbyl, C$_1$-C$_8$ hydrocarbyloxy, oxo, and the like, and/or on a secondary nitrogen atom (i.e., —NH—) of the ring by alkyl, aralkoxycarbonyl, alkanoyl, aryl or arylalkyl or on a tertiary nitrogen atom (i.e., =N—) by oxido and that is attached via a carbon atom. The tertiary nitrogen atom with three substituents can also attached to form a N-oxide [=N(O)—] group. Illustrative heterocyclic groups include piperazinyl, morpholinyl, tetrahydrofuranyl, isopyrrolyl, pyranyl, oxazinyl, dithiolyl, dioxazolyl and the like.

The term "heteroaryl", alone or in combination means a 5- or 6-membered aromatic ring-containing moiety or a fused ring system (radical) containing two or three rings that have carbon atoms and also one or more heteroatoms in the ring(s) such as sulfur, oxygen and nitrogen. Examples of such heterocyclic or heteroaryl groups are pyrrolidinyl, piperidyl, piperazinyl, morpholinyl, thiamorpholinyl, pyrrolyl, imidazolyl (e.g., imidazol-4-yl, 1-benzyloxycarbonylimidazol-4-yl, and the like), pyrazolyl, pyridyl, pyrazinyl, pyrimidinyl, furyl, tetrahydrofuryl, thienyl, triazolyl, oxazolyl, oxadiazoyl, triazolyl, thiadiazoyl, indolyl (e.g., 2-indolyl, and the like), quinolinyl, (e.g., 2-quinolinyl, 3-quinolinyl, 1-oxido-2-quinolinyl, and the like), isoquinolinyl (e.g., 1-isoquinolinyl, 3-isoquinolinyl, and the like), tetrahydroquinolinyl (e.g., 1,2,3,4-tetrahydro-2-quinolyl, and the like), 1,2,3,4-tetrahydroisoquinolinyl (e.g., 1,2,3,4-tetrahydro-1-oxo-isoquinolinyl, and the like), quinoxalinyl, β-carbolinyl, 2-benzofurancarbonyl, benzothiophenyl, 1-, 2-, 4- or 5-benzimidazolyl, and the like radicals.

The term "arC$_1$-C$_8$ hydrocarbyl", alone or in combination, means a hydrocarbyl radical as defined above in which one hydrogen atom is replaced by an aryl radical as defined above, such as benzyl, 2-phenylethyl and the like.

The term "arC$_1$-C$_8$ hydrocarbyloxycarbonyl", alone or in combination, means a radical of the formula arC1-C8 hydrocarbyl-O—C(O)— in which the term "arC1-C8 hydrocarbyl" has the significance given above. An example of an arC$_1$-C$_8$ hydrocarbyloxycarbonyl radical is benzyloxycarbonyl.

The term "aryloxy" means a radical of the formula aryl-O— in which the term aryl has the significance given above. The phenoxy radical is an exemplary aryloxy radical.

The terms "heteroarC$_1$-C$_8$ hydrocarbyl" and "heteroaryloxy" mean radicals structurally similar to arC$_1$-C$_8$ hydrocarbyloxy and aryloxy that are formed from heteroaryl radicals. Exemplary radicals include 4-picolinyl and 2-pyrimidinoxy, respectively.

The term "cyclohydrocarbylcarbonyl" means an acyl group derived from a monocyclic or bridged cyclohydrocarbylcarboxylic acid such as cyclopropanecarbonyl, cyclohexanecarbonyl, adamantanecarbonyl, and the like, or from a benz-fused monocyclic cyclohydrocarbylcarboxylic acid that is optionally substituted by, for example, alkanoylamino, such as 1,2,3,4-tetrahydro-2-naphthoyl, 2-acetamido-1,2,3, 4-tetrahydro-2-naphthoyl.

The terms "arhydrocarboyl" or "arC$_1$-C$_8$ hydrocarbylcarbonyl" mean an acyl radical derived from an aryl-substituted hydreocarbylcarboxylic acid such as phenylacetyl, 3-phenylpropionyl (hydrocinnamoyl), 4-phenylbutyryl, (2-naphthyl) acetyl, 4-chlorohydro-cinnamoyl, 4-aminohydrocinnamoyl, 4-methoxyhydro-cinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "cyclohydrocarbylhydrobarbyl-oxycarbonyl" means an acyl group of the formula cyclohydrocarbylhydrocarbyl-O—CO—. The term "aryloxyhydrocarboyl" means an acyl radical of the formula aryl-O-hydrocarboyl. The term "heterocyclooxycarbonyl" means an acyl group having the formula heterocyclo-O—CO— wherein heterocyclo is as defined above.

The term "heterocyclohydrocarboyl" is an acyl radical of the formula heterocyclo-substituted hydrocarbyl carboxylic acid. The term "heterocyclohydrocarbyloxycarbonyl" means an acyl radical of the formula heterocyclo-substituted hydrocarbyl-O—CO—. The term "heteroaryloxycarbonyl" means an acyl radical represented by the formula heteroaryl-O—CO— wherein heteroaryl has the significance given above.

The term "aminocarbonyl" (carboxamide) alone or in combination, means an amino-substituted carbonyl (carbamoyl) group derived from an amine reacted with a carboxylic acid wherein the amino (amido nitrogen) group is unsubstituted (—$NH_2$) or a substituted primary or secondary amino group containing one or two substituents selected from the group consisting of hydrogen, alkyl, aryl, aralkyl, cycloalkyl, cycloalkylalkyl radicals and the like, as recited. A hydroxamate is a N-hydroxycarboxamide.

The term "aminohydrocarboyl" means an acyl group derived from an amino-substituted hydrocarbylcarboxylic acid wherein the amino group can be a primary or secondary amino group containing substituents independently selected from hydrogen, alkyl, aryl, aralkyl, cycloalkyl, cycloalkylalkyl radicals and the like.

The term "halogen" means fluoride, chloride, bromide or iodide. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like.

The term "perfluorohydrocarbyl" means an alkyl group wherein each hydrogen has been replaced by a fluorine atom. Examples of such perfluorohydrocarbyl groups, in addition to trifluoromethyl above, are perfluorobutyl, perfluoroisopropyl, perfluorododecyl and perfluorodecyl.

The term "perfluorohydrocarbyloxy" alone or in combination, means a perfluoroalkyl ether radical wherein the term perfluoroalkyl is as defined above. Examples of such perfluorohydrocarboyloxy groups, in addition to trifluoromethoxy ($F_3C$—O—), are perfluorobutoxy, perfluoroisopropoxy, perfluorododecoxy and perfluorodecoxy.

The term "perfluorohydrocarbylthio" alone or in combination, means a perfluorohydrocarbyl thioether radical wherein the term perfluoroalkyl is as defined above. Examples of such perfluorohydrocarbylthio groups, in addition to trifluoromethylthio ($F_3C$—S—), are perfluorobutylthio, perfluoroisopropylthio, perfluorododecylthio and perfluorodecylthio.

The term "biologically-active sulfenic acid-containing protein" is used herein to describe a protein that contains a cysteine residue that can be oxidized to a sulfenic acid and exhibits biological activity when oxidized. Many such proteins are enzymes that contain an oxidizable cysteine at or near the active site of the enzyme. These enzymes are illustrated by aldol reductase (EC 1.1.1.21), peroxiredoxin (EC 1.11.1.15), and nitrile hydratase (EC 4.2.1.84). On the other hand, proteins such as actin that is generally thought of as a structural or mobility-providing protein, thereby providing physical functionality to a biological system, also have an oxidizable cysteine residue and participate in biologically active cellular signaling through that oxidized cysteine.

DETAILED DESCRIPTION OF THE INVENTION

The present invention contemplates the use of a boronic or borinic acid compound (derivative) or salt, hydrate or solvate thereof to inhibit the activity of a sulfenic acid-containing protein. As is seen from the structural formulas below, the phrase "a boronic or borinic acid compound (derivative)" and similar phrases are meant to include the acid forms as well as the ester forms as defined by those formulas. More specifically, the present invention contemplates contacting a biologically-active sulfenic acid-containing protein that is typically in an aqueous composition with an activity-inhibiting effective amount of a boronic or borinic acid compound of Formula I or salt, hydrate or solvate thereof, and maintaining that contact for a time sufficient to inhibit the activity of that protein. A biologically-active sulfenic acid-containing protein is often an enzyme, but need not be an enzyme. When that protein is an enzyme, the sulfenic acid that is involved with the biological activity to be inhibited is typically at the active site of the enzyme.

A contemplated compound of Formula I is illustrated hereinbelow:

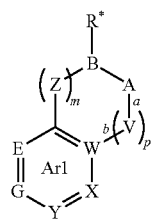

I wherein

A is oxygen (O) when p is 1 and bond a is present, or $R^7$ or $OR^7$ when bond a is absent and p is 0;

B is boron;

V is $CH_2$ when p is 1 and bonds a and b are present, and absent when p is 0 and bonds a and b are absent;

E is N, or $CR^2$;

G is N, or $CR^3$;

W is N, C, or $CR^4$;

X is N or $CR^5$;

Y is N or $CR^6$;

Z=O (oxygen) or $(CH_2)_nC(=O)O$, where n=0, 1 or 2, and m=0 or 1 such that Z is absent when m=0 and B is bonded directly to the aromatic or heteroaromatic ring, Ar1;

p=0 (zero) or 1, with the proviso that when p is 1, W is C, bonds a and b are present and m is 0, and when p is zero (0), all three of V, bond a and bond b are absent, and W is N or $CR^4$;

m=is 0 (zero) or 1, with the proviso that m is 0 or 1 when p is 1, and m is 1 when p is 0, with the further proviso that when m=1 at least one of A and R* is other than $OR^7$ and $OR^1$, respectively; and R* is $R^1$ or $OR^1$.

The $R^1$ and $R^7$ groups are selected independently from the group consisting of hydrido (hydrogen; H), optionally substituted $C_1$-$C_8$ hydrocarbyl, optionally substituted aryl, ar$C_1$-C8 hydrocarbyl, and optionally substituted heteroaryl. Contemplated optional substituents are themselves selected from the group of $C_1$-$C_8$ hydrocarbyl, aryl, ar$C_1$-$C_8$ hydrocarbyl, heteroaryl, heteroar$C_1$-$C_8$ hydrocarbyl, heterocyclyl, cyclohydrocarbyloxy, heterocyclyloxy, —C(O)-aryl, hydrocarbyloxy, aryloxy, heteroaryloxy, —OC(O)—($C_1$-$C_8$ hydrocarbyl), —$OCH_2CH_2OH$, —$O(CH_2)_3CO_2H$, 2-(morpholino) ethoxy, —$(CH_2)_kOH$ (where k=1, 2 or 3), —$CH_2NH_2$, —$CH_2NH(C_1$-$C_8$ hydrocarbyl), —$CH_2N(C_1$-$C_8$ hydrocarbyl)$_2$, halogen, formyl (—CHO), thioformyl (—CHS), —CH=NOH, —$CO_2H$, thiocarboxyl (—CSOH), sulfonyl (—$HSO_2$), $C_1$-$C_8$ hydrocarbylsulfonyl, arylsulfonyl, heteroarylsulfonyl, $C_1$-$C_8$ hydrocarbylsulfinyl, arylsulfinyl, heteroarylsulfinyl, —$CO_2$($C_1$-$C_8$ hydrocarbyl, —$CONH_2$, —$CONH$($C_1$-$C_8$ hydrocarbyl), —$CON$($C_1$-$C_8$ hydrocarbyl)$_2$, —OH, —SH, —S—($C_1$-$C_8$ hydrocarbyl), —S-aryl, —$SO_2$($C_1$-$C_8$ hydrocarbyl), —$SO_2N$($C_1$-$C_8$ hydrocarbyl)$_2$, $C_1$-$C_8$ hydrocarbylsulfonylamino (—$SO_2NH$ $C_1$-$C_8$ hydrocarbyl), aryl sulfonylamino, —$SO_2NH_2$, —$SO_3H$, —$SCF_3$, —CN, —$CHF_2$, —$CF_3$, —$NO_2$, amino (—$NH_2$), —NH($C_1$-$C_8$ hydrocarbyl), —N($C_1$-$C_8$ hydrocarbyl)$_2$, arylamino, diarylamino, —$NHSO_2$($C_1$-$C_8$ hydrocarbyl), —$CONH$($C_1$-$C_8$ hydrocarbyl), and —$CON$($C_1$-$C_8$ hydrocarbyl)$_2$.

The above-recited $R^2$, $R^3$, $R^4$, $R^5$ and $R^6$ groups are independently selected from the group consisting of hydrogen (hydrido; H), $C_1$-$C_8$ hydrocarbyl, aryl, ar$C_1$-$C_8$ hydrocarbyl, heteroaryl, heteroar$C_1$-$C_8$ hydrocarbyl, heterocyclyl, cyclohydrocarbyloxy, heterocyclyloxy, —C(O)-aryl, hydrocarbyloxy, aryloxy, heteroaryloxy, —OC(O)—($C_1$-$C_8$ hydrocarbyl), —$OCH_2CH_2OH$, —$O(CH_2)_3CO_2H$, 2-(morpholino)ethoxy, —$(CH_2)_kOH$ (where k=1, 2 or 3), —$CH_2NH_2$, —$CH_2NH$($C_1$-$C_8$ hydrocarbyl), —$CH_2N$($C_1$-$C_8$ hydrocarbyl)$_2$, halogen, formyl (—CHO), thioformyl (—CHS), —CH=NOH, —$CO_2H$, thiocarboxyl (—CSOH), sulfonyl (—$HSO_2$), $C_1$-$C_8$ hydrocarbylsulfonyl, arylsulfonyl, heteroarylsulfonyl, $C_1$-$C_8$ hydrocarbylsulfinyl, arylsulfinyl, heteroarylsulfinyl, —$CO_2$($C_1$-$C_8$ hydrocarbyl, —$CONH_2$, —$CONH$($C_1$-$C_8$ hydrocarbyl), —$CON$($C_1$-$C_8$ hydrocarbyl)$_2$, —OH, —SH, —S—($C_1$-$C_8$ hydrocarbyl), —S-aryl, —$SO_2$($C_1$-$C_8$ hydrocarbyl), —$SO_2N$($C_1$-$C_8$ hydrocarbyl)$_2$, $C_1$-$C_8$ hydrocarbyl-sulfonylamino (—$SO_2NH$ $C_1$-$C_8$ hydrocarbyl), aryl sulfonylamino, —$SO_2NH_2$, —$SO_3H$, —$SCF_3$, —CN, —$CHF_2$, —$CF_3$, —$NO_2$, amino (—$NH_2$), —NH($C_1$-$C_8$ hydrocarbyl), —N($C_1$-$C_8$ hydrocarbyl)$_2$, arylamino, diarylamino, —$NHSO_2$($C_1$-$C_8$ hydrocarbyl), —$CONH$($C_1$-$C_8$ hydrocarbyl), and —$CON$($C_1$-$C_8$ hydrocarbyl)$_2$. The $C_1$-$C_8$ hydrocarbyl, aryl, ar$C_1$-$C_8$ hydrocarbyl, heteroaryl, heteroar$C_1$-$C_8$ hydrocarbyl, cyclohydrocarbyl and heterocyclic groups in each of the $R^2$, $R^3$, $R^4$, $R^5$ and $R^6$ ($R^{2-6}$) substituents are themselves optionally substituted with one or more substituents selected from $C_1$-$C_8$ hydrocarbyl, aryl, ar$C_1$-$C_8$ hydrocarbyl, heteroaryl, heteroar$C_1$-$C_8$ hydrocarbyl, heterocyclyl, cyclohydrocarbyloxy, heterocyclyloxy, —C(O)-aryl, hydrocarbyloxy, aryloxy, heteroaryloxy, —OC(O)—($C_1$-$C_8$ hydrocarbyl), —$OCH_2CH_2OH$, —$O(CH_2)_3CO_2H$, 2-(morpholino)ethoxy, —$(CH_2)_kOH$ (where k=1, 2 or 3), —$CH_2NH_2$, —$CH_2NH$($C_1$-$C_8$ hydrocarbyl), —$CH_2N$($C_1$-$C_8$ hydrocarbyl)$_2$, halogen, formyl (—CHO), thioformyl (—CHS), —CH=NOH, —$CO_2H$, thiocarboxyl (—CSOH), sulfonyl (—$HSO_2$), $C_1$-$C_8$ hydrocarbylsulfonyl, arylsulfonyl, heteroarylsulfonyl, $C_1$-$C_8$ hydrocarbylsulfinyl, arylsulfinyl, heteroarylsulfinyl, —$CO_2$($C_1$-$C_8$ hydrocarbyl, —$CONH_2$, —$CONH$($C_1$-$C_8$ hydrocarbyl), —$CON$($C_1$-$C_8$ hydrocarbyl)$_2$, —OH, —SH, —S—($C_1$-$C_8$ hydrocarbyl), —S-aryl, —$SO_2$($C_1$-$C_8$ hydrocarbyl), —$SO_2N$($C_1$-$C_8$ hydrocarbyl)$_2$, $C_1$-$C_8$ hydrocarbylsulfonyl-amino (—$SO_2NH$ $C_1$-$C_8$ hydrocarbyl), aryl sulfonylamino, —$SO_2NH_2$, —$SO_3H$, —$SCF_3$, —CN, —$CHF_2$, —$CF_3$, —$NO_2$, amino (—$NH_2$), —NH($C_1$-$C_8$ hydrocarbyl), —N($C_1$-$C_8$ hydrocarbyl)$_2$, arylamino, diarylamino, —$NHSO_2$($C_1$-$C_8$ hydrocarbyl), —$CONH$($C_1$-$C_8$ hydrocarbyl), and —$CON$($C_1$-$C_8$ hydrocarbyl)$_2$.

Alternatively, one or more adjacent pairs of $R^2$, $R^3$, $R^4$, $R^5$ and $R^6$ (such as $R^2$ and $R^3$, or $R^3$ and $R^4$, $R^4$ and $R^5$, or $R^5$ and $R^6$) together with the atoms to which they are bonded form an optionally substituted mono- or bicyclic aromatic ring or heteroaromatic ring Ar2 that is fused to depicted ring Ar1.

In some embodiments of a method of the invention, the compounds of Formula I include those for which one or both of $R^1$ and $R^7$ is an optionally substituted aryl or heteroaryl group. In more specific embodiments for which one of $R^1$ and $R^7$ is optionally substituted aryl, one of $R^1$ and $R^7$ is optionally substituted heteroaryl to provide thereby mixed aryl-heteroaryl substituents. In a still more specific embodiment in which one of $R^1$ and $R^7$ is optionally substituted aryl and one of $R^1$ and $R^7$ is optionally substituted heteroaryl, the optionally substituted heteroaryl is optionally substituted pyridyl. Yet more specific embodiments for which one $R^1$ and $R^7$ is optionally substituted pyridyl include those for which one of $R^1$ and $R^7$ is optionally substituted phenyl.

In more particular embodiments, an optionally substituted aryl group such as phenyl or heteroaryl group such as pyridyl is substituted by a moiety selected from the group consisting of $C_1$-$C_8$ hydrocarbyl, aryl, substituted aryl, ar$C_1$-$C_8$ hydrocarbyl, —$(CH_2)_kOH$ (where k=1, 2 or 3), —$CH_2NH_2$, —$CH_2NH$($C_1$-$C_8$ hydrocarbyl), —$CH_2N$($C_1$-$C_8$ hydrocarbyl)$_2$, —$CO_2H$, —$CO_2$($C_1$-$C_8$ hydrocarbyl), —$CONH_2$, —$CONH$($C_1$-$C_8$ hydrocarbyl), —$CON$($C_1$-$C_8$ hydrocarbyl)$_2$, —OH, $C_1$-$C_8$ hydrocarbyloxy, aryloxy, —SH, —S—($C_1$-$C_8$ hydrocarbyl), —S-aryl, —$SO_2$($C_1$-$C_8$ hydrocarbyl), —$SO_2N$($C_1$-$C_8$ hydrocarbyl)$_2$, —$SO_2NH$($C_1$-$C_8$ hydrocarbyl), —$SO_2NH_2$, —$SO_3H$, —$SCF_3$, —CN, halogen, —$CF_3$, —$NO_2$, amino (—$NH_2$), —NH($C_1$-$C_8$ hydrocarbyl), —N($C_1$-$C_8$ hydrocarbyl)$_2$, —$NHSO_2$($C_1$-$C_8$ hydrocarbyl), —$NHSO_2$($C_1$-$C_8$ hydrocarbyl), —$OCH_2CH_2NH_2$, —$OCH_2CH_2NH$($C_1$-$C_8$ hydrocarbyl), —$OCH_2CHN_2$($C_1$-$C_8$ hydrocarbyl)$_2$, oxazolidin-2-yl, and $C_1$-$C_8$ hydrocarbyl substituted oxazolidin-2-yl.

More particular embodiments of a contemplated compound include those in which the optionally substituted phenyl is phenyl substituted by a moiety selected from the group consisting of hydrogen, halogen, and hydrocarbyl, and, more particularly, those wherein the halogen is chloro or fluoro, still more particularly, those wherein the halogen is chloro or fluoro and the hydrocarbyl is methyl.

One preferred group of compounds of Formula I are the compounds of Formula A, shown below. Starting from a compound of Formula I, p is zero and bond a and bond b are absent, W is N (nitrogen), or $CR^4$, where m, A, B, E, G, X, Y, Z and R* are as before defined.

A

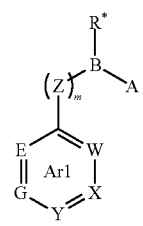

In a first preferred embodiment of a compound of Formula A, m is one, and Z is O (oxygen) to provide a compound of Formula A-1, below, where A, B, E, G, W, X, Y and R* are as before defined.

A-1

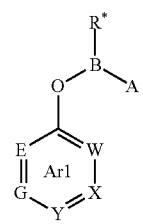

A particularly preferred compound of Formula A-1 is a compound of Formula A-1-1, in which $R^2$ and $R^3$ together with the atoms to which they are bonded (atoms E and G) form an aromatic or heteroaromatic ring Ar2 as is shown below in Formula A-1-1. In ring Ar2,

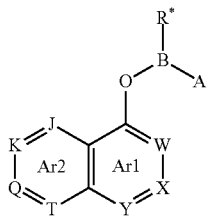

A-1-1 the ring atoms J, K, Q and T are:

J is N, or $CR^8$;

K is N, or $CR^9$;

Q is N, or $CR^{10}$; and

T is N, or $CR^{11}$, with the proviso that no more than two of J, K, Q and T can be N (nitrogen), and the remaining A, B, R*, W, X, and Y are as previously defined.

In one more preferred embodiment of a compound of Formula A-1-1, J is N (nitrogen), and A, B, O, W, X, Y, K, Q, R* and T are as defined before, which provides a compound of Formula II shown below. A

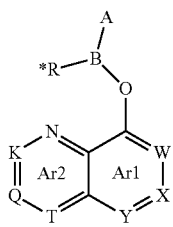

II compound of Formula II can be a derivative of a boronic acid or of a borinic acid. It is preferred that a compound of Formula II be a borinic acid compound, so that A is $R^7$ and R* is $R^1$.

In a second preferred embodiment of a compound of Formula I, m is one, Z is $(CH_2)_nC(=O)O$, p is zero (0), so V, bond a and bond b are absent to provide a compound of Formula A-2, below, where A, B, E, G, O, X, Y, W, n, and R* are as before described, and C is carbon and H is hydrogen.

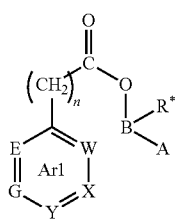

A-2

In a particularly preferred embodiment of a compound of Formula A-2, W is N (nitrogen) to provide a compound of Formula III, below, where A, B, C, H, O, E, G, X, Y, n, and R* are as before described.

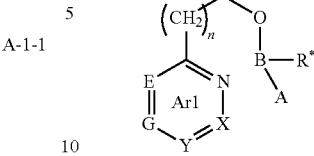

III

Alternatively, a compound of Formula III can be viewed as a compound of Formula A in which Z is $(CH_2)_nC(=O)O$, W is N (nitrogen), A, B, C, E, G, H, O, X, Y, n, and R* are as before described.

As can be seen, a compound of Formula III can be a boronic acid or a borinic acid. It is preferred that a compound of Formula III be a borinic acid compound, so that A is $R^7$ and R* is $R^1$.

In another preferred embodiment of a compound of Formula I, m is 0 (zero) so that Z is absent and B is bonded directly to ring Ar1, A is O (oxygen), W is C (carbon), and A, B, E, G, R*, W, X, Y, V, bond a and bond b are as defined before, providing a compound of Formula B, below.

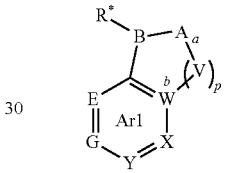

B

In one preferred embodiment of a compound of Formula B, A is O (oxygen), W is C, V is $CH_2$, p is 1 and bonds a and b are present, with B, E, G, X, Y, and R* being as before described to provide a compound of Formula IV, below.

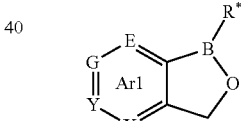

IV

A compound of Formula IV can be a borinic acid or a boronic acid compound, but preferably, R* is $OR^1$ and a compound of Formula IV is a boronic acid.

In yet another preferred embodiment of a compound of Formula B, based on the structure of Formula I, m is 0 (zero), A is $OR^7$, p is 0 (zero), V is absent and bond a and bond b are absent, W is N or $CR^4$, with E, G, X, Y, and R* being as before described to provide a compound of Formula V, below.

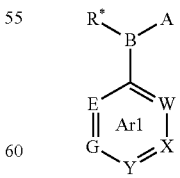

V

A compound of Formula V can be a borinic acid or a boronic acid, but preferably, R* is $OR^1$ and A is $OR^7$ so that a compound of Formula V is a boronic acid compound.

One particularly preferred borinic acid is a compound of Formula II. In that compound, based on a compound of Formula I, J is N (nitrogen), m is 1, Z is oxygen (O), R* is $R^1$ and A is $R^7$, W is $CR^4$, X is $CR^5$, Y is $CR^6$, K is $CR^9$, Q is $CR^{10}$, and T is $CR^{11}$, so that a contemplated borinic acid compound corresponds to Formula II-1, below.

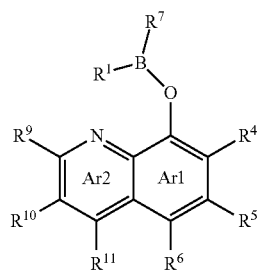

II-1

In some preferred embodiments of a contemplated compound of Formula II-1, $R^1$ and $R^7$ are selected independently from the group consisting of optionally substituted alkenyl, optionally substituted optionally substituted aryl, optionally substituted heteroaryl, and optionally substituted heterocyclic. Contemplated $R^4$, $R^5$, $R^6$ and $R^9$, $R^{10}$ and $R^{11}$ substituents are selected independently from the group consisting of hydrogen (hydrido; H), $C_1$-$C_8$ hydrocarbyl, aryl, ar$C_1$-$C_8$ hydrocarbyl, heteroaryl, heteroar$C_1$-$C_8$ hydrocarbyl, heterocyclyl, cyclohydrocarbyloxy, heterocyclyloxy, —C(O)-aryl, $C_1$-$C_8$ hydrocarbyloxy, aryloxy, heteroaryloxy, —OC(O)— $C_1$-$C_8$ hydrocarbyl, —OCH$_2$CH$_2$OH, —O(CH$_2$)$_3$CO$_2$H, 2-(morpholino)ethoxy, —(CH$_2$)$_k$OH (where k=1, 2 or 3), —CH$_2$NH$_2$, —CH$_2$NH(C$_1$-$C_8$ hydrocarbyl), —CH$_2$N(C$_1$-$C_8$ hydrocarbyl)$_2$, halogen, formyl (—CHO), thioformyl (—CHS), —CH=NOH, —CO$_2$H, thiocarboxyl (—CSOH), sulfonyl (—HSO$_2$), $C_1$-$C_8$ hydrocarbylsulfonyl, arylsulfonyl, heteroarylsulfonyl, $C_1$-$C_8$ hydrocarbylsulfinyl, arylsulfinyl, heteroarylsulfinyl, —CO$_2$(C$_1$-$C_8$ hydrocarbyl), —CONH$_2$, —CONH(C$_1$-$C_8$ hydrocarbyl), —CON(C$_1$-$C_8$ hydrocarbyl)$_2$, —OH, —SH, —S— $C_1$-$C_8$ hydrocarbyl, —S-aryl, —SO$_2$(C$_1$-$C_8$ hydrocarbyl), —SO$_2$N(C$_1$-$C_8$ hydrocarbyl)$_2$, $C_1$-$C_8$ hydrocarbyl sulfonylamino [—SO$_2$NH(C$_1$-$C_8$ hydrocarbyl)], aryl sulfonylamino, —SO$_2$NH$_2$, —SO$_3$H, —SCF$_3$, —CN, —CHF$_2$, —CF$_3$, —NO$_2$, amino (—NH$_2$), —NH(C$_1$-$C_8$ hydrocarbyl), —N(C$_1$-$C_8$ hydrocarbyl)$_2$, arylamino, diarylamino, —NHSO$_2$(C$_1$-$C_8$ hydrocarbyl), —CONH(C$_1$-$C_8$ hydrocarbyl) and —CON(C$_1$-$C_8$ hydrocarbyl)$_2$. The $C_1$-$C_8$ hydrocarbyl, aryl, ar$C_1$-$C_8$ hydrocarbyl, heteroaryl, heteroar$C_1$-$C_8$ hydrocarbyl, cyclohydrocarbyl and heterocyclic groups in all of the $R^4$, $R^5$, $R^6$ and $R^9$, $R^{10}$ and $R^{11}$ substituents are themselves optionally substituted with a substituent selected from hydrogen (hydrido; H), $C_1$-$C_8$ hydrocarbyl, aryl, ar$C_1$-$C_8$ hydrocarbyl, heteroaryl, heteroar$C_1$-$C_8$ hydrocarbyl, heterocyclyl, cyclohydrocarbyloxy, heterocyclyloxy, —C(O)-aryl, hydrocarbyloxy, aryloxy, heteroaryloxy, —OC(O)—(C$_1$-$C_8$ hydrocarbyl), —OCH$_2$CH$_2$OH, —O(CH$_2$)$_3$CO$_2$H, 2-(morpholino)ethoxy, —(CH$_2$)$_k$OH (where k=1, 2 or 3), —CH$_2$NH$_2$, —CH$_2$NH(C$_1$-$C_8$ hydrocarbyl), —CH$_2$N(C$_1$-$C_8$ hydrocarbyl)$_2$, halogen, formyl (—CHO), thioformyl (—CHS), —CH=NOH, —CO$_2$H, thiocarboxyl (—CSOH), sulfonyl (—HSO$_2$), $C_1$-$C_8$ hydrocarbylsulfonyl, arylsulfonyl, heteroarylsulfonyl, $C_1$-$C_8$ hydrocarbylsulfinyl, arylsulfinyl, heteroarylsulfinyl, —CO$_2$(C$_1$-$C_8$ hydrocarbyl), —C(O)NH$_2$, —C(O)NH(C$_1$-$C_8$ hydrocarbyl), —C(O)N(C$_1$-$C_8$ hydrocarbyl)$_2$, —OH, —SH, —S—(C$_1$-$C_8$ hydrocarbyl), —S-aryl, —SO$_2$(C$_1$-$C_8$ hydrocarbyl), —SO$_2$N(C$_1$-$C_8$ hydrocarbyl)$_2$, $C_1$-$C_8$ hydrocarbylsulfonylamino (—SO$_2$NH C$_1$-$C_8$ hydrocarbyl), aryl sulfonylamino, —SO$_2$NH$_2$, —SO$_3$H, —SCF$_3$, —CN, —CHF$_2$, —CF$_3$, —NO$_2$, amino (—NH$_2$), —NH(C$_1$-$C_8$ hydrocarbyl), —N(C$_1$-$C_8$ hydrocarbyl)$_2$, arylamino, diarylamino, —NHSO$_2$(C$_1$-$C_8$ hydrocarbyl), —C(O)NH(C$_1$-$C_8$ hydrocarbyl), and —C(O)N(C$_1$-$C_8$ hydrocarbyl)$_2$.

In some embodiments, one or both of $R^1$ and $R^7$ is optionally substituted aryl or optionally substituted heteroaryl. In more specific embodiments, $R^1$ is optionally substituted aryl and $R^7$ is optionally substituted aryl. In yet more specific embodiments, $R^1$ and $R^7$ independently are optionally substituted phenyl. More preferred embodiments include those for which $R^1$ and $R^7$ independently are phenyl substituted with at least one moiety selected from the group consisting of halo, hydroxy, thio, amino, formyl, thioformyl, carboxy, carbamoyl, thiocarbamoyl, cyano, optionally substituted $C_1$-$C_8$ hydrocarbyloxy, $C_1$-$C_8$ hydrocarbylthio, aryloxy, arylthio, $C_1$-$C_8$ hydrocarbylamino, di($C_1$-$C_8$ hydrocarbyl)amino, arylamino, diarylamino, and $C_1$-$C_8$ hydrocarbyl-carbonyloxy. Contemplated optional substituents for these substituents are selected from hydrogen (hydrido; H), $C_1$-$C_8$ hydrocarbyl, aryl, ar$C_1$-$C_8$ hydrocarbyl, heteroaryl, heteroar$C_1$-$C_8$ hydrocarbyl, heterocyclyl, cyclohydrocarbyloxy, heterocyclyloxy, —C(O)-aryl, hydrocarbyloxy, aryloxy, heteroaryloxy, —OC(O)—(C$_1$-$C_8$ hydrocarbyl), —OCH$_2$CH$_2$OH, —O(CH$_2$)$_3$CO$_2$H, 2-(morpholino)ethoxy, —(CH$_2$)$_k$OH (where k=1, 2 or 3), —CH$_2$NH$_2$, —CH$_2$NH(C$_1$-$C_8$ hydrocarbyl), —CH$_2$N(C$_1$-$C_8$ hydrocarbyl)$_2$, halogen, formyl (—CHO), thioformyl (—CHS), —CH=NOH, —CO$_2$H, thiocarboxyl (—CSOH), sulfonyl (—HSO$_2$), $C_1$-$C_8$ hydrocarbylsulfonyl, arylsulfonyl, heteroarylsulfonyl, $C_1$-$C_8$ hydrocarbylsulfinyl, arylsulfinyl, heteroarylsulfinyl, —CO$_2$(C$_1$-$C_8$ hydrocarbyl), —C(O)NH$_2$, —C(O)NH(C$_1$-$C_8$ hydrocarbyl), —C(O)N(C$_1$-$C_8$ hydrocarbyl)$_2$, —OH, —SH, —S—(C$_1$-$C_8$ hydrocarbyl), —S-aryl, —SO$_2$(C$_1$-$C_8$ hydrocarbyl), —SO$_2$N(C$_1$-$C_8$ hydrocarbyl)$_2$, $C_1$-$C_8$ hydrocarbylsulfonylamino (—SO$_2$NH C$_1$-$C_8$ hydrocarbyl), aryl sulfonylamino, —SO$_2$NH$_2$, —SO$_3$H, —SCF$_3$, —CN, —CHF$_2$, —CF$_3$, —NO$_2$, amino (—NH$_2$), —NH(C$_1$-$C_8$ hydrocarbyl), —N(C$_1$-$C_8$ hydrocarbyl)$_2$, arylamino, diarylamino, —NHSO$_2$(C$_1$-$C_8$ hydrocarbyl), —C(O)NH(C$_1$-$C_8$ hydrocarbyl), and —C(O)N(C$_1$-$C_8$ hydrocarbyl)$_2$.

Of the latter embodiments, preferred compounds of Formula II-1, include those wherein $R^1$ and $R^7$ independently are phenyl substituted with at least one moiety selected from the group consisting of halo, hydroxy, thio, amino, formyl, thioformyl, carboxy, carbamoyl, thiocarbamoyl, cyano, optionally substituted $C_1$-$C_8$ hydrocarbyloxy, $C_1$-$C_8$ hydrocarbylthio, aryloxy, arylthio, $C_1$-$C_8$ hydrocarbylamino, di($C_1$-$C_8$ hydrocarbylamino), arylamino, diarylamino, and $C_1$-$C_8$ hydrocarbylcarbonyloxy.

Still more particular compounds include those where additionally $R^4$, $R^5$, $R^6$ and $R^9$, $R^{10}$ and $R^{11}$ are selected independently from the group consisting of hydrogen, halo, hydroxy, thio, amino, formyl, thioformyl, carboxy, carbamoyl, thiocarbamoyl, cyano, optionally substituted hydrocarbyloxy, $C_1$-$C_8$ hydrocarbylthio, aryloxy, arylthio, $C_1$-$C_8$ hydrocarbylamino, di($C_1$-$C_8$ hydrocarbylamino), arylamino, diarylamino, and $C_1$-$C_8$ hydrocarbyl-carbonyloxy. More preferably, $R^4$, $R^5$, $R^6$ and $R^9$, $R^{10}$ and $R^{11}$ independently are hydrogen, halo, or amino.

Other embodiments of the present invention include the use of compounds having the structure of Formula II-1 in which $R^4$, $R^5$, $R^6$ and $R^9$, $R^{10}$ and $R^{11}$ independently are hydrogen, halo, or amino and $R^1$ and $R^7$ independently are phenyl substituted with at least one moiety selected from the group consisting of halo, hydroxy, and amino.

Particularly preferred embodiments are those in which the compound is (3-fluorophenyl)-(4-chlorophenyl)borinic acid 5,7-dichloro-8-hydroxyquinoline ester, bis(3-chlorophenyl) borinic acid 2-amino-8-hydroxyquinoline ester or (3-chlorophenyl) (3,4-dimethoxyphenyl)borinic acid 8-hydroxyquinoline ester.

Another particularly preferred borinic acid is a compound of Formula III. In this embodiment, starting from a compound of Formula I, m is one, Z is $(CH_2)_nC(=O)O$, n is 0 (zero), W is N (nitrogen), R* is $R^1$ and A is $R^7$ so that a borinic acid compound of Formula III where E is $CR^2$, G is $CR^3$, X is $CR^5$, and Y is $CR^6$ corresponds to Formula III-1.

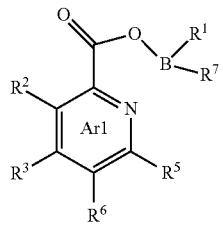

III-1

In some embodiments of the invention, a compound of Formula III-1 includes those for which one of $R^1$ and $R^7$ is optionally substituted aryl. In more specific embodiments, the compounds of Formula III-1 include those for which both $R^1$ and $R^7$ are optionally substituted aryl, and more preferably are optionally substituted phenyl.

Yet more specific embodiments are those wherein one of $R^1$ and $R^7$ is an optionally substituted phenyl and $R^2$, $R^3$, $R^5$ and $R^6$ are selected independently from the group consisting of hydrogen, hydroxy, $C_1$-$C_8$ hydrocarbyloxy, amino, and carboxy. In still more specific embodiments in which both of $R^1$ and $R^7$ are optionally substituted phenyl, $R^2$, $R^3$, $R^5$ and $R^6$ are selected independently from the group consisting of hydrogen, hydroxy, $C_1$-$C_8$ hydrocarbyloxy, amino, and carboxy. The optionally substituted phenyl of $R^1$ and/or $R^7$ is phenyl substituted by a moiety selected from the group consisting of hydrogen, $C_1$-$C_8$ hydrocarbyl, aryl, substituted aryl, ar$C_1$-$C_8$ hydrocarbyl, —$(CH_2)_kOH$ (where k=1, 2 or 3), —$CH_2NH_2$, —$CH_2NH(C_1$-$C_8$ hydrocarbyl), —$CH_2N(C_1$-$C_8$ hydrocarbyl)$_2$, —$CO_2H$, —$CO_2(C_1$-$C_8$ hydrocarbyl), —$C(O)NH_2$, —$C(O)NH(C_1$-$C_8$ hydrocarbyl, $C(O)N(C_1$-$C_8$ hydrocarbyl)$_2$, —OH, $C_1$-$C_8$ hydrocarbyloxy, aryloxy, —SH, —S— $C_1$-$C_8$ hydrocarbyl, —S-aryl, —$SO_2(C_1$-$C_8$ hydrocarbyl, —$SO_2N(C_1$-$C_8$ hydrocarbyl)$_2$, —$SO_2NH(C_1$-$C_8$ hydrocarbyl), —$SO_2NH_2$, —$SO_3H$, —$SCF_3$, —CN, halogen, —$CF_3$, —$NO_2$, amino (—$NH_2$), —$NH(C_1$-$C_8$ hydrocarbyl), —$N(C_1$-$C_8$ hydrocarbyl)$_2$, —$NHSO_2(C_1$-$C_8$ hydrocarbyl), —$NHSO_2(C_1$-$C_8$ hydrocarbyl), —$OCH_2CH_2NH_2$, —$OCH_2CH_2NH(C_1$-$C_8$ hydrocarbyl), —$OCH_2CHN_2(C_1$-$C_8$ hydrocarbyl)$_2$, oxazolidin-2-yl, and $C_1$-$C_8$ hydrocarbyl substituted oxazolidin-2-yl.

Among those compounds of Formula III-1, more preferred compounds include those where both of $R^1$ and $R^7$ are optionally substituted phenyl, $R^2$, $R^3$, $R^5$ and $R^6$ are selected independently from the group consisting of hydrogen, hydroxy, $C_1$-$C_8$ hydrocarbyloxy, amino, or carboxy. Each of the optionally substituted phenyls is phenyl substituted by a moiety selected from the group consisting of those in the immediately preceding paragraph.

More specific embodiments include those in which at least one of $R^2$, $R^3$, $R^5$ and $R^6$ is hydroxy or amino, and, still more specifically, where $R^5$ is hydroxy and $R^2$, $R^3$ and $R^6$ are hydrogen. Of these latter compounds, more specific compounds include those for which the optionally substituted phenyl is phenyl substituted by a moiety that is hydrogen, halogen or $C_1$-$C_8$ hydrocarbyl.

Other more specific compounds having the structure shown in Formula III-1 are those for which $R^5$ is hydroxy and $R^2$, $R^3$ and $R^6$ are hydrogen and both of $R^1$ and $R^7$ are optionally substituted phenyl where the optionally substituted phenyl is phenyl substituted by a moiety selected from the group consisting of halogen, and $C_1$-$C_8$ hydrocarbyl and the halogen is chloro. More specific compounds are those in which $R^5$ is hydroxy and $R^2$, $R^3$ and $R^6$ are hydrogen and both of $R^1$ and $R^7$ are optionally substituted phenyl where the optionally substituted phenyl is phenyl substituted by a moiety selected from the group consisting of hydrogen, halogen, and $C_1$-$C_8$ hydrocarbyl and the halogen is chloro and the $C_1$-$C_8$ hydrocarbyl is methyl ($C_1$). Of these compounds, particularly useful is (bis(3-chloro-4-methylphenyl)boryloxy)(3-hydroxypyridin-2-yl)methanone, including its pharmaceutically acceptable salts, hydrates, or solvates.

In still other embodiments of the invention, the compounds shown in Formula III-1 include those where both of $R^1$ and $R^7$ are optionally substituted phenyl, $R^2$, $R^3$, $R^5$ and $R^6$ are selected independently from the group consisting of hydrogen, hydroxy, $C_1$-$C_8$ hydrocarbyloxy, amino, and carboxy. The optionally substituted phenyl is phenyl substituted by a moiety selected from the group consisting of $C_1$-$C_8$ hydrocarbyl, aryl, substituted aryl, aryl $C_1$-$C_8$ hydrocarbyl, —$(CH_2)_kOH$ (where k=1, 2 or 3), —$CH_2NH_2$, —$CH_2NH$ ($C_1$-$C_8$ hydrocarbyl), —$CH_2N(C_1$-$C_8$ hydrocarbyl)$_2$, —$CO_2H$, —$CO_2(C_1$-$C_8$ hydrocarbyl), —$C(O)NH_2$, —$C(O)NH(C_1$-$C_8$ hydrocarbyl), —$C(O)N(C_1$-$C_8$ hydrocarbyl)$_2$, —OH, $C_1$-$C_8$ hydrocarbyloxy, aryloxy, —SH, —S— $C_1$-$C_8$ hydrocarbyl, —S-aryl, —$SO_2(C_1$-$C_8$ hydrocarbyl), —$SO_2N$ ($C_1$-$C_8$ hydrocarbyl)$_2$, —$SO_2NH(C_1$-$C_8$ hydrocarbyl), —$SO_2NH_2$, —$SO_3H$, —$SCF_3$, —CN, halogen, —$CF_3$, —$NO_2$, amino (—$NH_2$), —$NH(C_1$-$C_8$ hydrocarbyl), —$N(C_1$-$C_8$ hydrocarbyl)$_2$, —$NHSO_2(C_1$-$C_8$ hydrocarbyl), —$NHSO_2(C_1$-$C_8$ hydrocarbyl), —$OCH_2CH_2NH_2$, —$OCH_2CH_2NH(C_1$-$C_8$ hydrocarbyl), —$OCH_2CHN(C_1$-$C_8$ hydrocarbyl)$_2$, oxazolidin-2-yl, and $C_1$-$C_8$ hydrocarbyl substituted oxazolidin-2-yl, and $R^5$ is hydroxy, $R^2$ amino, and $R^3$ and $R^6$ are hydrogen.

Of these latter compounds, useful compounds include those where the optionally substituted phenyl is phenyl substituted by a moiety selected from the group consisting of hydrogen, halogen, and hydrocarbyl. More specific useful embodiments are those where the halogen is chloro. Of these compounds, the compound (bis(3-chlorophenyl)boryloxy) (6-amino-3-hydroxypyridin-2-yl)methanone, including its pharmaceutically acceptable salts, hydrates, and solvates, are preferred.

One preferred boronic acid compound is a compound of Formula I in which m is 0 (zero), A is O (oxygen), V is $CH_2$, W is C (carbon), p is 1, bonds a and b are present, R* is $OR^1$, E is $CR^2$, G is $CR^3$, X is $CR^5$, and Y is $CR^6$ to provide a compound of Formula IV-1, below.

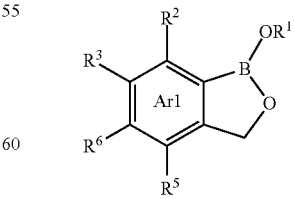

IV-1

In one particularly preferred compound of Formula IV-1, each of $R^1$, $R^2$, $R^3$, $R^5$, and $R^6$ is hydrogen. That compound has the formula IV-1A, shown below, and is referred to as BOXY.

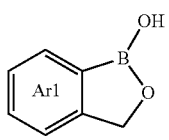
IV-1A

Another boronic acid derivative compound of a compound of Formula I is a compound in which m is 0 (zero) so B is bonded directly to the aromatic ring Ar1, W is CH, p is 0 and bonds a and b are absent so V is absent, A is $OR^7$, R* is $OR^1$, E is CH, G is $CR^3$, X is $CR^5$, and Y is $CR^6$ to provide a compound of Formula V-1, below.

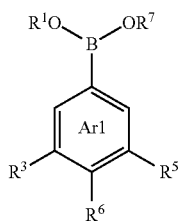
V-1

In one preferred compound of Formula V-1, $R^7$ and $R^1$ are both H. Each of $R^3$, $R^5$, and $R^6$ is independently selected from a like-numbered R group of a compound of Formula I. More preferably, each of $R^3$, $R^5$, and $R^6$ is independently selected from the group consisting of nitro (—$NO_2$), halogen (fluoro, chloro or bromo), $C_1$-$C_8$ hydrocarbyl, —$CHF_2$, —$CF_3$, $C_1$-$C_8$ hydrocarbyloxy, aryloxy and di-$C_1$-$C_8$ hydrocarbylamino [—$N(C_1$-$C_8$ hydrocarbyl$)_2$]. More preferably still, only one or none of $R^3$, $R^5$, and $R^6$ is other than hydrogen.

Formulas of illustrative compounds of Formula V-1 are shown below as Formulas V-1A-V-1I.

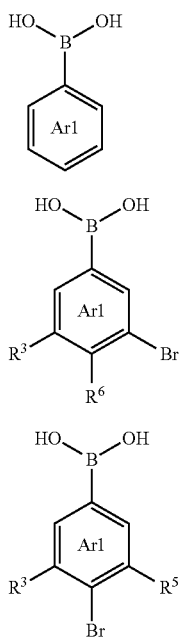

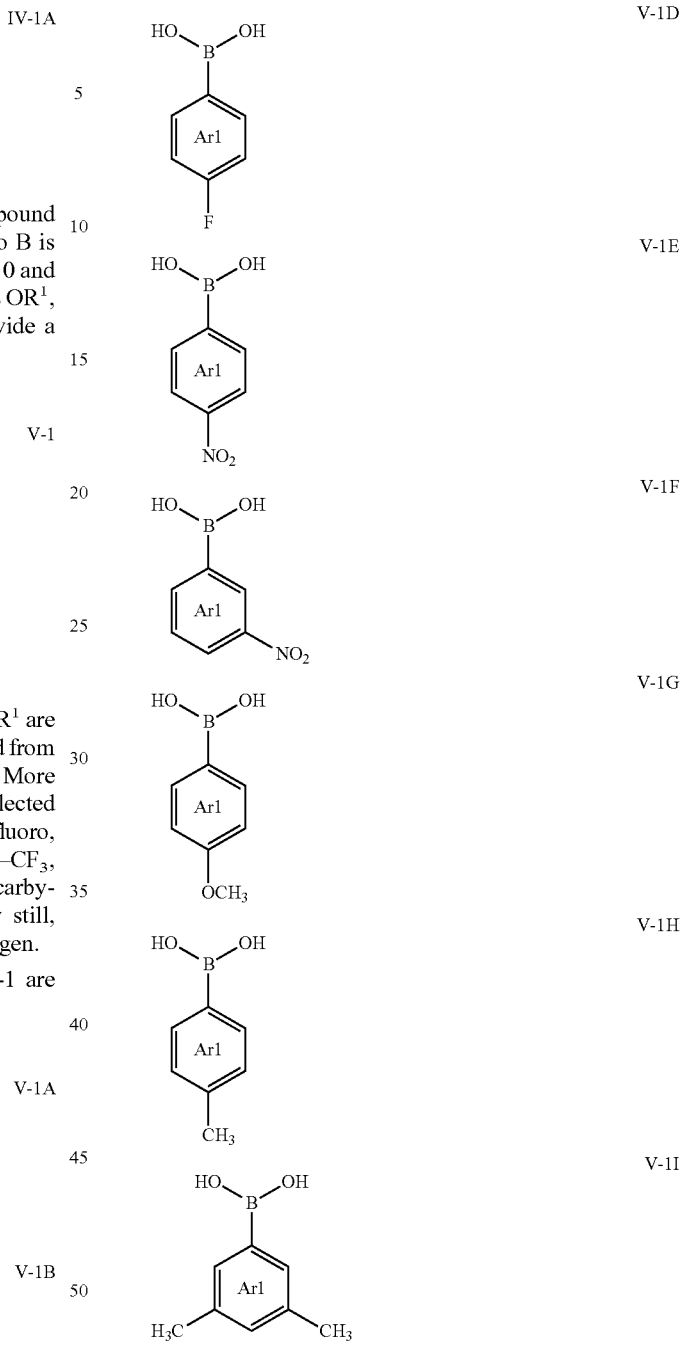

A compound of Formula I, along with one or more preferred sub-genera of compounds and preferred specific compounds, is disclosed in one or more U.S. Pat. No. 8,168,614, U.S. Pat. No. 8,115,026, U.S. Pat. No. 8,039,450, U.S. Pat. No. 7,816,344, U.S. Pat. No. 7,767,657, U.S. Pat. No. 7,652,000, U.S. Pat. No. 7,582,621, U.S. Pat. No. 7,465,836, U.S. Pat. No. 7,393,856, and U.S. Pat. No. 7,390,806. The preparation of these compounds is also disclosed in an above-noted patent. These disclosures are incorporated by reference. In addition, several boronic acid compounds are available from Alfa Aesar North America, Ward Hill, Mass.

Pharmaceutical Composition

A compound of Formula I can be provided for use by itself, or as a salt, hydrate, or solvate thereof. As is well known, a hydrate is typically a solid form that contains one or more water molecules or a fraction of a water molecule as when one water molecule is shared by two molecules of a compound. A solvate is similar to a hydrate except that a water molecule is replaced by one or more or a fractional amount of a solvent molecule(s) other than water. A preferred salt form is a pharmaceutically acceptable salt.

Although substituent groups can provide an acid or base functionality, a contemplated compound of Formulas I can be an acid and used in the form of a pharmaceutically acceptable base addition salt derived from an inorganic or organic base. Examples include salts with alkali metals or alkaline earth metals, such as sodium, potassium, calcium or magnesium (inorganic bases) or with organic bases or basic quaternary ammonium salts.

Other compounds useful in this invention that contain base functionalities such as amine groups can also form salts. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

The reader is directed to Berge, *J. Pharm. Sci.* 1977 68(1): 1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

A contemplated pharmaceutical composition contains a biological activity-inhibiting effective amount effective amount of a compound Formula I or a pharmaceutically acceptable salt thereof dissolved or dispersed in a physiologically tolerable carrier or diluent. Such a composition can be used to interact with a biologically active sulfenic acid-containing protein in vitro as in a cell culture or aqueous composition, or in vivo as in a living, host mammal in diagnosed need.

A contemplated composition is typically administered a plurality of times over a period of days. More usually, a contemplated composition is administered a plurality of times in one day. The biological activity-inhibiting amount of compound can therefore be present in a single dose, or can be achieved over a period of time through multiple contacts or administrations.

A contemplated pharmaceutical composition can be administered orally (perorally), parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

An injectable preparation, for example, a sterile injectable aqueous or oleaginous suspension can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

A sterile solution can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, a compound used in this invention is ordinarily combined with one or more excipients such as adjuvants appropriate to the indicated route of administration. If administered per os, the compounds can be admixed with lactose, sucrose, starch powder, cellulose esters of alkanoic acids, cellulose hydrocarbyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal in diagnosed need of treatment and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where in vitro contact is contemplated, a culture of cells from an illustrative mammal is often utilized, or the sulfenic acid-containing protein whose activity is to be inhibited can be present dissolved or suspended in an aqueous medium.

Preferably, the pharmaceutical composition is in unit dosage form. In such form, the composition is divided into unit doses containing appropriate quantities of the compound of Formula I. The unit dosage form can be a packaged prepara-

Example 1

Binding Studies

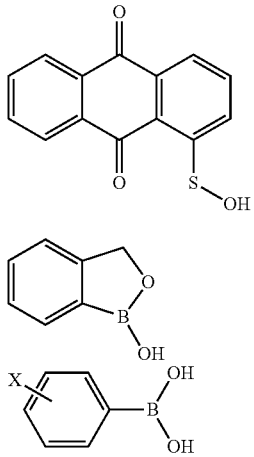

2b. X = 4-nitro
2c. X = 3-nitro
2d. X = 3-bromo
2e. X = 4-bromo
2f. X = 4-fluoro
2g. X = H
2h. X = 4-methoxy 1. Materials Reverse-osmosis purified water was further deionized to 18.2 MΩ·cm using a Millipore® filtration apparatus. The double deionized water (ddH$_2$O) was used for all the studies described below.

1-Chloroanthraqunone (98%), sodium sulfide (anhydrous), bromine (liquid, 99.8%), 2-(hydroxymethyl)benzeneboronic acid hemiester (98+%; 2A), 4-nitrobenzeneboronic acid (95%; 2b), 4-bromo-benzeneboronic acid (97+%; 2e), and 4-fluorobenzene-boronic acid (97%; 2f) were obtained from Alfa Aesar and used without further purification. 3-Bromobenzene-boronic acid (98+%; 2d) and 4-methoxybenzeneboronic acid (98%; 2h) were purchased from Lancaster Synthesis. Sodium hydroxide (≥98%), 200 proof anhydrous ethanol, 5,5-dimethyl-1,3-cyclohexanedione (95%; dimedone), dithiothreitol (DTT), chloroform, 3-nitrobenzeneboronic acid (≥98%; 2c), and phenylboronic acid (95%; 2 g) were obtained from Sigma Aldrich. Dimedone was recrystallized from ethanol/water mixture to ensure high purity. Deuterium oxide (99.9 atom % D) and acetonitrile-d$_3$ (99.8 atom % D) were from Cambridge Isotope Laboratories, Inc. Potassium hydroxide (min. 85%), acetonitrile (99.9%, low water), and anhydrous methanol were used as supplied from EMD. Sulfur was obtained from Fisher Scientific. NaOH solutions (of various concentrations) were prepared with ddH$_2$O and titrated against 1N or N/2 Fisher certified standard HCl solution to determine the exact concentrations. pH (H$_3$O$^+$ concentrations) values were measured using an Accumet model 13-620-300 standard combination electrode calibrated with VWR certified standard aqueous buffers (pH=4, 7, 10).

2. General Protocols

Initial binding studies were carried out with Fries' acid (anthraquinone-1-sulfenic acid, 1). Tis compound was synthesized according to a published procedure. [Fries, *Chem. Ber.* 1912 45:2965-2973.] The NMR, UV-vis, and mass spectroscopy data for the prepared Fries' acid are consistent with the structure and the literature data. [Fries, *Chem. Ber.* 1912 45:2965-2973; Kice et al., *J. Org. Chem.* 1989 54:4198-4203.]

The acid dissociation constants (pK$_a$ values) of the sulfenic acid 1 and the boronic acids were determined from half-neutralization technique where the ratio of [1 or 2]:[NaOH]=2:1. The pK$_a$ values were determined in 15% and 70% (v/v) acetonitrile-ddH$_2$O mixture, with concentrations of 1 or 2 ranging between 5-10 mM. The final volume of the solutions is 5 mL. The averaged pK$_a$ values from duplicate measurements are reported, and used for analysis.

It should be noted that the pK$_a$ values determined this way are not corrected for the change in the autoprotolysis constant of the solution due to mix solvent system. Although the actual correction factor (correcting the observed pH reading as standardized by aqueous buffers to various compositions of acetonitrile and water) is unknown, the same correction factor would be applied to all the compounds measured this way as long as they are in the same 15% (v/v) acetonitrile-water systems. Therefore, the trend observed here is valid. Also, it is expected that the actual correction factor in 15% (v/v) acetonitrile-water systems is small. When comparison can be made, the pK$_a$ values obtained from half-neutralization method in 15% (v/v) acetonitrile-water mixture are similar to the pK$_a$ values reported in water (there seems to be a small constant offset of about 0.4 unit between acetonitrile-water mixture and water). [Tomsho et al., *ACS Med. Chem. Lett.*, 2011 3:48-52]

When 2 mM of 1 was mixed with 2 mM of sodium hydroxide (NaOH) to generate the sodium salt in 15% (v/v) acetonitrile-ddH$_2$O mixture, the pH value of the mixture was found to be ~7 using a pH-indicator strip. When the above mixture was mixed with equal molar (2 mM) of 2A, 2e, or 2g, the pH of the resulting solution was found to be about 6-7. Under these concentrations, where substantial amount of 1:2 complex should be formed, an unchanged pH value indicates very little hydroxide being generated upon complex formation. This is consistent with the formation of a tetrahedral boron adduct of 1:2. If the trigonal boron complex [1:2-$^-$OH] was the major adduct species, the pH of the mixture should be much higher due to the release of hydroxide (eg. 2 mM of hydroxide being released; pH>11).

3. Spectrophotometric Titrations

Spectrophotometric titrations were performed in 15% (v/v) acetonitrile-ddH$_2$O. In a typical study, stock solutions of deprotonated 1 in 100% acetonitrile and boronic acid 2 in 15% (v/v) acetonitrile-ddH$_2$O mixture were prepared just prior to the titration.

Conventional phosphate and Good's buffers were found to interfere with the binding of boronic acids 2 to sulfenic acid 1.

The titration studies were performed using a Cary 100 Bio UV/vis spectrophotometer thermostated at 22° C. First, the absorbance of a UV/vis cell (path length of 1 cm; scanning between 350-700 nm) containing 0.8 mM of the sodium salt of 1 (by mixing with one equivalent of NaOH) in 15% (v/v) acetonitrile-ddH$_2$O was recorded. Subsequently, aliquots of stock solution of 2 (also in 15% (v/v) acetonitrile-ddH$_2$O) were added stepwise, while the absorption spectrum (350-700 nm) of the mixture was recorded after each addition. Each titration study was completed within 10 minutes.

The biggest change in the UV/vis spectrum due to 1:2 adduct formation appeared at 468 nm. After correcting for dilution (due to the addition of 2) and the intrinsic absorbances of the cell and solvents, the absorbance value at 468 nm was plotted against the concentration of compound 2 {[2]} to generate a binding curve.

Except for 2b, solutions containing 2:1 ratio of boronic acid 2 and NaOH do not have significant absorbance between 420 to 700 nm. For the titration between compounds 1 and 2b, the recorded absorbance (468 nm) values were also corrected for the intrinsic absorbance of 2b using the extinction coefficient value ($\lambda = 4.2 \pm 0.3$ $M^{-1}$ $cm^{-1}$ in 15% (v/v) acetonitrile-water at 22° C.) for 2b. The absorbance vs. [2] plots were fitted to a universal binding equation (eq. 1, below) to yield the individual dissociation constants ($K_d$, reciprocal of the binding constants) for complexes of 1:2 in solution.

For boronic acids 2A and 2d, similar spectrophotometric titrations with sulfenic acid 1 were also performed in 70% (v/v) acetonitrile-water mixture to probe the effect of solution composition on adduct formation. The reactions between sulfenic acid 1 and dimedone or DTT were also monitored in a similar manner as described above.

Reversibility studies were also performed where the 1:2d adduct (0.8 mM of sodium salt of 1 and 4.5 mM of 2d was generated in situ, and treated with 4.5 mM of NaOH to recover the original UV/vis absorption spectrum of the unbound deprotonated 1 in solution. Similar reversibility studies were done with boronic acids 2A and 2c too.

$$Y = B + A(1 - ((1 + K_B^*[S] + [X]^*K_B - C))/(2K_B)/[S]) \quad \text{eq. (1)}$$

where:

$$C = \{1 + 2K_B^*[S] + 2^*[X]^*K_B + K_B^{2*}[S]^2 - 2^*K_B^{2*}[X][S] + [X]^{2*}K_B^2\}^{0.5}$$

Equation (1) is a universal binding expression [Liu et al., *J. Am. Chem. Soc.* 2010 132: 3561-3573] derived from the equations for equilibrium binding and for conservation of mass by using the commercially available MAPLE software [Maple V Release 5, Waterloo Maple, Inc., Waterloo, Ontario, Canada.] In equation (1), B represents the initial absorbance value when [X] is zero; [X] is the concentration of the species represented on the x-axis; A is the change in absorbance between [X]=0 and [X]=infinitely large; [S] is the concentration of the sodium salt of sulfenic acid 1; and $K_B$ is the inverse of the dissociation constant, $K_d$, for complex 1:2. Y is the corrected absorbance value (measured value) at 468 nm after accounting for the dilution effect during titration, the intrinsic absorbance of the solvent mixture, and absorbance of the UV-cell.

The averaged dissociation constants obtained from titrations are summarized in Table 1, below. The dissociation constants are similar between various boronic acids used. Also, solvent composition has minimal effect on the formation of complex 1:2. The $pK_a$ value of sulfenic acid 1 was found to be 7.61±0.02 in 15% (v/v) acetonitrile-water, which is similar to the value of 7.51 reported in Kice et al., *J. Org. Chem.* 1989 54:4198-4203, and 8.6±0.1 in 70% acetonitrile-water.

TABLE 1

| | $pK_a$ in 15% acetonitrile-water at 22° C. | Averaged-log ($K_d$) in 15% acetonitrile-water at 22° C. | Averaged-log ($K_d$) in 70% acetonitrile-water at 22° C. |
|---|---|---|---|
| 2A | 7.8 ± 0.1[1] | 3.8 ± 0.1 | 3.90 ± 0.02 |
| 2b | 7.39 ± 0.05 | 3.6 ± 0.1 | ND |
| 2c | 8.13 ± 0.01 | 3.53 ± 0.01 | ND |
| 2d | 8.55 ± 0.0 | 3.8 ± 0.1 | 4.0 ± 0.1 |
| 2e | 9.1 ± 0.1 | 3.90 ± 0.04 | ND |
| 2f | 9.4 ± 0.02 | 3.80 ± 0.01 | ND |
| 2g | 9.5 ± 0.06 | 3.7 ± 0.2 | 3.96 ± 0.04 |
| 2h | 10.13 ± 0.02 | 3.81 ± 0.01 | ND |

[1]Averaged $pK_a$ value from half neutralization method in 70% (v/v) acetonitrile-water = 10.2 ± 0.1.
ND = Not done.

4. Reactivity with DTT and Dimedone

Addition of dimedone to a solution containing the sodium salt of sulfenic acid 1 in 15% (v/v) acetonitrile-water mixture resulted in significant decrease of the characteristic peak of the deprotonated 1 at 676 nm. A new peak around 487 nm also increased in intensity with each addition of dimedone stock solution. These spectral changes are consistent with the nucleophilic attack on dimedone by the sulfenic acid [Allison, *Acc. Chem. Res.* 1976 9:293-299]. However, due to the formation of precipitates from the chemical reaction between dimedone and 1, a reasonable titration curve was not possible.

Reaction between dithiothreitol (DTT) and sulfenic acid 1 was also observed by UV/vis spectrophotometry. Mixing DTT and the sodium salt of 1 resulted in the characteristic peak of the deprotonated 1 at 676 nm to decrease. A new peak at 460 nm also started to appear when DTT was immediately mixed with 1. However, a significant constant global absorbance decrease was observed soon after the reaction between DTT and 1. This was a non-reversible process, probably due to some redox processes between compound 1 and DTT.

5. Reversibility Titration

A complex formation reversibility study between the sodium salt of 1 and 2d in 15% (v/v) acetonitrile-water mixture at 22° C. was carried out. The initial solution contained 0.8 mM of the sodium salt of 1. Mixing 2d (final [2d]=4.5 mM) with 0.8 mM of the sodium salt of 1 resulted in absorbance value decrease at ~676 nm (characteristic peak of deprotonated 1) [Kice et al., *J. Org. Chem.* 1989, 54:4198-4203] and absorbance value increase centered at 468 nm. Addition of 4.5 mM of NaOH regenerated the initial absorption curve.

These results suggest that the formation of complex 1:2d is a reversible process that can be reversed by hydroxide. Hydroxide can displace the bound sulfenic acid on the boron. Similar reversibility results were found using 2A instead of 2d. The absorbance values were corrected to account for dilution due to the addition of stock solutions of 2d and NaOH.

6. General Isothermal Calorimetry (ITC)

ITC experiments were done using a MICROCAL™ isothermal titration calorimeter Auto-iTC200 (GE) while the raw data were analyzed by OneSites model using the packaged Origin 7 [Origin 7, OriginLab Corporation, Northampton, Mass., USA.] In a typical study, 400 µL of solution containing 2 mM of the sodium salt of 1 in 15% (v/v) acetonitrile-ddH$_2$O was loaded into the reaction chamber thermostatted at 25° C. The injection syringe was loaded with 200 µL of solution containing 10-20 mM of a Compound 2 in 15% acetonitrile-ddH$_2$O at 25° C. The samples were prepared immediately prior to each study.

Typical reaction protocol involved 25 injections (1.6 µL aliquots, over 3 seconds) with 80 seconds spacing time, reference power of 10 µCal/sec, 300× stir speed, and high feedback mode. Duplicate runs were done and the calculated values were averaged. Each ITC run usually took about 30 minutes to complete. Before the actual ITC titrations, the system (injection syringes and reacting chambers) was thoroughly rinsed with 15% (v/v) acetonitrile-water mixture.

It is expected that some of the sulfenic acid 1 might have degraded during this time period, resulting in lower concentration of 1 (lower than the origin concentration) available for titration. A control ITC study was performed by titrating 15% (v/v) acetonitrile-water mixture into a solution of deprotonated 1 (with NaOH). Another set of control studies involved titrating solutions of 2 into 15% (v/v) acetonitrile-water mixture. None of the control ITC studies showed any signs of heat release due to bond formation.

Table 2, below, summarizes the data obtained from ITC studies. The $K_d$ values obtained from ITC studies agree well with those obtained from spectrophotometric titrations. The discrepancy found between the values obtained by two different means are expected, especially considering the limitations of the methodologies used. For example, the ITC studies took longer to perform and have a 30 minute pre-rinse cycle preceded every study. These conditions can contribute to higher degree of degradation of Compound 1 in solution.

TABLE 2

|  | 2A | 2d | 2g |
|---|---|---|---|
| pKa in 15% acetonitrile-water | 7.80 | 8.48 | 9.38 |
| Averaged $K_d$ from spectrophotometric titrations (M) | $1.58 \times 10^{-4}$ | $1.58 \times 10^{-4}$ | $2.0 \times 10^{-4}$ |
| Averaged $K_d$ from ITC (M) | $(1.4 \pm 0.3) \times 10^{-4}$ | $(5.2 \pm 1.1) \times 10^{-5}$ | $(1.1 \pm 0.1) \times 10^{-4}$ |
| Averaged ΔH (kcal/mol) | $-6.6 \pm 0.3$ | $-4.7 \pm 0.4$ | $-9.3 \pm 0.8$ |
| Averaged ΔS (cal/mol/K) | $-4.4 \pm 0.3$ | $-3.8 \pm 1.9$ | $-12 \pm 6$ |

7. Mass Spectrometry

Time-of-flight (TOF) mass spectrometry (MS) detection of the 1:2 adducts was performed using electrospray negative ionization method (ESI-). The samples were injected through directing sample infusion. Typical study conditions involved using 40-60V cone voltage, 120-150° C., and 1500-1800V capillary voltage.

A mixture containing equal concentrations of 1 (as sodium salt) and 2 in 15% (v/v) acetonitrile-water mixture was prepared immediately prior to injection for MS analysis. The concentrations of 1 and 2 ranged from 0.1-0.5 mM.

The raw data were analyzed using MassLynx MS software [MassLynx MS Software, Waters Corporation, Milford, Mass., USA], which was also used to generate the expected isotopic pattern for data comparison. In all cases, peaks corresponding to the mass of the adduct $[1-H^+:2]^{-1}$ were observed. The temperature of the system and the capillary voltage were adjusted to examine how these two factors influence the detectable species. Lowering the temperature and the capillary voltage were found to increase the amount of detectable adduct; consistent with the expected behavior of complex formation.

Use of a solution containing 0.1 mM of 1, 0.1 mM of 2f, and 0.1 mM of NaOH in 15% acetonitrile-water mixture provided peaks corresponding to the complex ($C_6H_6BFO_2$: $C_{14}H_7O_3S^-$; $[2f:1-H]^{-1}$) that were found to match the predicted isotopic pattern. The predicted and the experimental peaks for ($C_6H_6BBrO_2$:$C_{14}H_7O_3S^-$; $[2e:1-H]^{-1}$) are noted to be at m/z=455.0, 457.0 (major). For complex $[2A:1-H]^{-1}$, the isotopic peak pattern for the species $C_7H_7BO_2$:$C_{14}H_7O_3S^-$ at m/z=389.1 (major) was found at m/z=389.3 (major). For complex $[2b:1-H]^{-1}$, the expected isotopic peak pattern for the species $C_6H_6BNO_4$:$C_{14}H_7O_3S^-$ at m/z=422.1 (major) was found at m/z=422.2 (major). For complex $[2d:1-H]^{-1}$, the expected isotopic peak pattern for the species $C_6H_6BBrO_2$:$C_{14}H_7O_3S^-$ at m/z=455.0, 457.0 (major) was found at m/z=455.0, 457. (major). For complex $[2g:1-H]^{-1}$, the expected expected isotopic peak pattern for the species $C_6H_7BO_2$:$C_{14}H_7O_3S^-$ at m/z=377.1 (major) was found at m/z=377.3 (major).

Other species detected by MS included $[1-H]^{-1}$, $[1-H+O]^{-1}$, $[2-H]^{-1}$, $[1:1-H]^{-1}$, $[1+O: 1-H]^{-1}$, $[2:2-H]^{-1}$, and $[1:2-H+O]^{-1}$.

8. $^{11}$B Nuclear Magnetic Resonance (NMR) Spectrometry $^{11}$B NMR characterization of the 1:2 adduct was done at 96.2 MHz and 298K on a Bruker™ CDPX-300 liquid state NMR spectrometer. All chemical shifts were referenced to $Et_2O.BF_3$ in $CDCl_3$. The studies involved measuring the $^{11}$B NMR peak positions of 2A or 2d in 15% (v/v) acetonitrile-$d_3$ in deuterium oxide in quartz NMR tubes. The final volume inside the quartz NMR tubes was 800 μL. Spectra were collected using a 4.9 μs 90° pulse, 488 ms FID acquisition time, and a 1 s acquisition delay. The sweep width was set to 87.2 ppm and the temperature was kept at 298° K. Line broadening adjustment was set at 10 Hz.

For comparison, four separate $^{11}$B NMR spectrum were taken for boronic acid 2A: a) 10 mM of 2A and 10 mM of HCl, b) 10 mM of 2A and 20 mM of NaOH, c) 10 mM 2A and 5 mM of NaOH, d) 6 mM of 2A, 6 mM of sodium salt of 1, and 3 mM of NaOH, and e) 10 mM of 2A, 5 mM of sodium salt of 1, and 5 mM of NaOH. Similar sets of spectra were also collected for boronic acid Compound 2d. The raw data were processed using ACD/Labs 1D NMR processor software [ACD/Labs 1D NMR processor, version 12.0, Advanced Chemistry Development, Inc., Toronto, ON, Canada, www.acdlabs.com, 2012].

The peak positions of the trigonal 2A and the tetrahedral 2A:$^-$OH species were 32.9 ppm and 8.3 ppm, respectively. A very broad peak resulted for a solution containing equal amounts of 2A and 2A:$^-$OH (19.9 ppm). Mixing equal amounts of 2A and the deprotonated sulfenic acid 1 yielded a $^{11}$B NMR peak at 8.8 ppm, which is consistent with the formation of the tetrahedral $[1:2A-H]^{-1}$ complex in solution. Similar observations were found for the complex formation between 1 and 2d (Table 3, below). It should be noted that the $^{11}$B peak for the 1:2 adduct is sharp when [1]=[2]. This is consistent with the majority of boronic acid 2 being trapped as the 1:2 complex, instead of a large fractions of 2 being in equilibrium between the bound (as 1:2 adduct) and the free species (e.g., [2]=2·[1]). The latter situation should lead to a much broader $^{11}$B NMR peak, which was confirmed to be true.

TABLE 3

| Composition | Shift (ppm) | Composition | Shift (ppm) |
|---|---|---|---|
| 10 mM 2A<br>10 mM HCl | 32.9 | 10 mM 2d<br>10 mM HCl | 28.8 |
| 10 mM 2A<br>20 mM NaOH | 8.3 | 10 mM 2d<br>20 mM NaOH | 2.6 |
| 10 mM 2A<br>5 mM NaOH | 19.9 | 10 mM 2d<br>5 mM NaOH | 16.3 |
| 6 mM 2A<br>6 mM sodium salt of 1<br>3 mM NaOH | 8.8[1] | 6 mM 2d<br>6 mM sodium salt of 1<br>3 mM NaOH | 8.7 |

TABLE 3-continued

| Composition | Shift (ppm) | Composition | Shift (ppm) |
|---|---|---|---|
| 10 mM 2A<br>5 mM sodium<br>salt of 1<br>5 mM NaOH | 12.02 | 10 mM 2d<br>5 mM sodium<br>salt of 1<br>5 mM NaOH | 10.9 |

[1] sharp peak; when [sodium salt of 1] = 5 mM, [2A] = 10 mM, and [NaOH] = 5 mM, a very broad $^{11}$B peak appeared at 12 ppm.

Example 2

Enzymatic Inhibition of Nitrile Hydratase

Nitrile hydratase (NHase) catalyzes the hydration of nitriles, making it an important industrial enzyme for the production of acrylamide. NHases are metalloenzymes that contain either a non-heme $Fe^{3+}$ or non-corrin $Co^{3+}$ in the active site. Mechanistic studies have shown that NHases (from *Rhodococcus erythropolis* N771) utilize a sulfenic acid moiety, $\alpha Cys^{114}$-SOH, to activate an attacking solvent molecule. [Hashimoto et al., *J. Biol. Chem.* 2008 283:36617-36623.] The presence of the sulfenic acid is important for the catalysis. The results shown below illustrate that catalytic activity of NHase drops in the presence of boronic acids, exhibiting greater enzymatic inhibition with higher concentrations of boronic acids.

Here, the catalytic efficiency of the iron-based NHase from *Rhodococcus erythropolis* AJ270 (purchased from Prozomix Limited, Station court, Haltwhistle, Northumberland, NE49 9HN, UK; see, proxomix.com) was assayed in the presence of a known sulfenic acid trap (dimedone) and four boronic acid derivatives. The chosen assay [Sari et al., *J. Inorg. Biochem.* 2007 101:614-622] was the conversion of 2-nitro-5-thiocyanatobenzoic acid (NCTB) into formamide and 5-mercapto-2-nitrobenzoic acid.

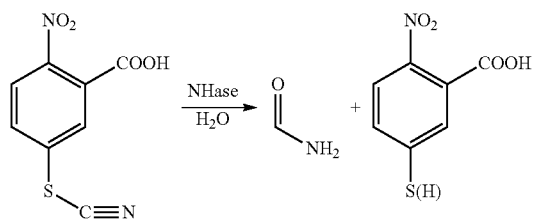

Assay Conditions:

The freeze-dried powder from Prozomix was shipped at room temperature and stored at −20° C. upon arrival. The enzyme was reconstituted at 20 mg/mL in 50 mM phosphate buffer (pH 7.0) with 40 mM butyric acid. These were similar conditions to those described in the Prozomix protocol, the main difference being the use of phosphate buffer instead of Tris buffer; by itself, NHase prepared in Tris had the same reactivity as samples prepared in phosphate buffer. The solution was exposed to 400 W white light for 25 minutes on ice to permit for photo-reactivation of the enzyme.

The kinetic studies were conducted by diluting the stock solution of NHase into de-ionized distilled water (dd$H_2O$) to get at about 0.33 mg/mL of freeze-dried NHase powder provided by Prozomix (used without further manipulation) in solution. Appropriate amounts of PBA (phenyl boronic acid; 2g), BOXY ((2-hydroxylmethyl)-benzeneboronic acid hemiester; 2A), 3BrB (3-bromobenzeneboronic acid; 2d), or dimedone were added to the mixtures so that the final concentrations of the boronic acids/dimedone were 0, 0.5, 1.0, 2.0, or 2.5 mM.

After permitting the newly composed mixtures to sit at room temperature (at about 23° C.) for five minutes, NCTB was added so that the final NCTB concentration equalled 1 mM. The final volume of the mixtures was 1 mL in UV-cells with 1 cm path length. The final concentration of the phosphate buffer was 3.6 mM. The progress of the reaction (release of the thiolate product at 412 nm; extinction coefficient at 412 nm=13600/M/cm) [Sari et al., *J. Inorg. Biochem.* 2007 101:614-622] was monitored using a Cary 100 Bio UV-vis spectrophotometer at 23° C. The rates of the reaction were determined from fitting the first 4 minutes of the absorbance vs. time traces to a standard linear equation. The activity values were calculated as nmol of thiolate product generated per minute per mg of freeze-dried NHase powder. The reaction rates are reported below in Table 4, below, as averages of duplicate kinetic studies.

TABLE 4

Summary of NHase reactivity

| | Average rate (abs/min) | Rate relative to NHase | Activity (nmol/min/mg) |
|---|---|---|---|
| [B]*/[Dimedone] = 0.5 mM | | | |
| NHase** | 0.0045 ± 0.0001 | 100% | 1.004 |
| PBA (2g) | 0.0043 ± 0.0004 | 96% | 0.968 |
| BOXY (2A) | 0.0039 ± 0.0002 | 87% | 0.870 |
| 3BrB (2d) | 0.0039 ± 0.0004 | 87% | 0.878 |
| Dimedone | 0.00274 ± 0.00006 | 61% | 0.611 |
| [B]*/[Dimedone] = 1.0 mM | | | |
| NHase** | 0.00453 ± 0.00009 | 100% | 1.109 |
| PBA (2g) | 0.0041 ± 0.0002 | 91% | 1.006 |
| BOXY (2A) | 0.0034 ± 0.0002 | 74% | 0.826 |
| 3BrB (2d) | 0.00369 ± 0.00009 | 81% | 0.903 |
| Dimedone | 0.0017 ± 0.0004 | 37% | 0.406 |
| [B]*/[Dimedone] = 2.0 mM | | | |
| NHase** | 0.0044 ± 0.0001 | 100% | 0.977 |
| PBA (2g) | 0.00382 ± 0.00004 | 87% | 0.851 |
| BOXY (2A) | 0.00266 ± 0.00008 | 61% | 0.592 |
| 3BrB (2d) | 0.00348 ± 0.0004 | 79% | 0.775 |
| Dimedone | 0 | 0%*** | 0 |
| [B]*/[Dimedone] = 2.5 mM | | | |
| NHase** | 0.0046 ± 0.0002 | 100% | 1.127 |
| PBA (2g) | 0.0038 ± 0.0001 | 83% | 0.931 |
| BOXY (2A) | 0.00205 ± 0.00009 | 45% | 0.502 |
| 3BrB (2d) | 0.00319 ± 0.0007 | 69% | 0.782 |
| Dimedone | 0 | 0% | 0 |

*[B] = [boronic acid]
**does not contain boronic acid or dimedone.
***No detectable product formation in 7 minutes.

Results

The above data (Table 4) show a systematic decrease in the NHase reactivity with increasing amounts of PBA (2g), BOXY (2A), 3BrB (2d), or dimedone. The inhibition of NHase by dimedone (a common trap/probe for sulfenic acids) confirms the requirement of a cysteine sulfenyl group (Cys-SOH) for the catalysis.

Among the boronic acids examined, 2A seems to be the most effective. It is known from small molecule model systems that phosphate and Goods (e.g. Tris buffer) buffers greatly hinder the binding of boronic acids to sulfenyl groups. Unfortunately, buffer is required to stabilize NHase. Therefore, the inhibitory effectiveness of boronic acids for NHase is expected to be greater with lower or zero phosphate buffer.

It is known from small molecule model systems that phosphate and Goods (e.g. Tris) buffers greatly hinder the binding of boronic acids to sulfenyl groups. Unfortunately, buffer is required to stabilize isolated NHase. Therefore, the effectiveness of boronic acids for NHase inhibition is expected to be greater with lower or zero phosphate buffer. In addition, we found that 3.6 mM of buffer is sufficient to maintain the same NHase activity as if the enzyme were present in a higher buffer concentration such as 50 mM suggested by published procedures. Although lowering the buffer concentration is advantageous in maximizing the interaction between the boron compounds and the sulfenic acid moiety, low buffer concentration makes it difficult to maintain the pH value of the system when the concentration of a compound 2 molecule is greater than about 2.5 mM.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A method of inhibiting the biologic activity of a biologically-active sulfenic acid-containing enzyme that comprises the step of contacting said enzyme with an activity-inhibiting effective amount of a boronic acid or borinic acid compound of Formula V or a salt, hydrate, or solvate thereof, and maintaining that contact for a time sufficient to inhibit the activity of that enzyme

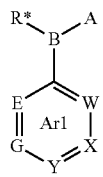

V wherein
A is OR$^7$,
E is N, or CR$^2$;
G is N, or CR$^3$;
W is N, or CR$^4$;
X is N or CR$^5$;
Y is N or CR$^6$;
R* is R$^1$ or OR$^1$;
R$^1$ and R$^7$ are selected independently from the group consisting of hydrido, optionally substituted C$_1$-C$_8$ hydrocarbyl, optionally substituted aryl, arC$_1$-C$_8$ hydrocarbyl, and optionally substituted heteroaryl, wherein said optional substituents are selected from the group consisting of C$_1$-C$_8$ hydrocarbyl, aryl, arC$_1$-C$_8$ hydrocarbyl, heteroaryl, heteroarC$_1$-C$_8$ hydrocarbyl, heterocyclyl, cyclohydrocarbyloxy, heterocyclyloxy, —C(O)-aryl, hydrocarbyloxy, aryloxy, heteroaryloxy, —OC(O)—(C$_1$-C$_8$ hydrocarbyl), —OCH$_2$CH$_2$OH, —O(CH$_2$)$_3$CO$_2$H, 2-(morpholino)ethoxy, —(CH$_2$)$_k$OH (where k=1, 2 or 3), —CH$_2$NH$_2$, —CH$_2$NH(C$_1$-C$_8$-hydrocarbyl), —CH$_2$N(C$_1$-C$_8$ hydrocarbyl)$_2$, halogen, formyl, thioformyl, —CH=NOH, —CO$_2$H, thiocarboxyl, sulfonyl, C$_1$-C$_8$ hydrocarbyl-sulfonyl, arylsulfonyl, heteroarylsulfonyl, C$_1$-C$_8$-hydrocarbylsulfinyl, arylsulfinyl, heteroaryl-sulfinyl, —CO$_2$(C$_1$-C$_8$-hydrocarbyl, —C(O)NH$_2$, —C(O)NH(C$_1$-C$_8$-hydrocarbyl), —CON(C$_1$-C$_8$ hydrocarbyl)$_2$, —OH, —SH, —S—(C$_1$-C$_8$-hydrocarbyl), —S-aryl, —SO$_2$(C$_1$-C$_8$-hydrocarbyl), —SO$_2$N(C$_1$-C$_8$-hydrocarbyl)$_2$, C$_1$-C$_8$-hydrocarbyl-sulfonylamino, aryl-sulfonylamino, —SO$_2$NH$_2$, —SO$_3$H, —SCF$_3$, —CN, CHF$_2$, —CF$_3$, —NO$_2$, amino, —NH(C$_1$-C$_8$-hydrocarbyl, —N(C$_1$-C$_8$-hydrocarbyl)$_2$, arylamino, diarylamino, —NHSO$_2$(C$_1$-C$_8$-hydrocarbyl), —C(O)NH(C$_1$-C$_8$-hydrocarbyl), and —C(O)N(C$_1$-C$_8$-hydrocarbyl)$_2$;

R$^2$, R$^3$, R$^4$, R$^5$ and R$^6$ are independently selected from the group consisting of hydrogen (hydrido), C$_1$-C$_8$ hydrocarbyl, aryl, arC$_1$-C$_8$-hydrocarbyl, heteroaryl, heteroarC$_1$-C$_8$-hydrocarbyl, heterocyclyl, cyclohydrocarbyloxy, heterocyclyloxy, —C(O)-aryl, hydrocarbyloxy, aryloxy, heteroaryloxy, —OC(O)—(C$_1$-C$_8$-hydrocarbyl), —OCH$_2$CH$_2$OH, —O(CH$_2$)$_3$CO$_2$H, 2-(morpholino)ethoxy, —(CH$_2$)$_k$OH (where k=1, 2 or 3), —CH$_2$NH$_2$, —CH$_2$NH(C$_1$-C$_8$-hydrocarbyl), —CH$_2$N(C$_1$-C$_8$ hydrocarbyl)$_2$, halogen, formyl, thioformyl, —CH=NOH, —CO$_2$H, thiocarboxyl, sulfonyl, C$_1$-C$_8$-hydrocarbyl-sulfonyl, arylsulfonyl, heteroarylsulfonyl, C$_1$-C$_8$-hydrocarbylsulfinyl, arylsulfinyl, heteroarylsulfinyl, —CO$_2$(C$_1$-C$_8$-hydrocarbyl), —C(O)NH$_2$, —C(O)NH(C$_1$-C$_8$-hydrocarbyl), —CON(C$_1$-C$_8$-hydrocarbyl)$_2$, —OH, —SH, —S—(C$_1$-C$_8$-hydrocarbyl), —S-aryl, —SO$_2$(C$_1$-C$_8$-hydrocarbyl), —SO$_2$N(C$_1$-C$_8$-hydrocarbyl)$_2$, C$_1$-C$_8$-hydrocarbyl-sulfonylamino, aryl-sulfonylamino, —SO$_2$NH$_2$, —SO$_3$H, —SCF$_3$, —CN, —CHF$_2$, —CF$_3$, —NO$_2$, amino, —NH(C$_1$-C$_8$-hydrocarbyl), —N(C$_1$-C$_8$-hydrocarbyl)$_2$, arylamino, diarylamino, —NHSO$_2$(C$_1$-C$_8$-hydrocarbyl), —CONH(C$_1$-C$_8$-hydrocarbyl), and —C(O)N(C$_1$-C$_8$-hydrocarbyl)$_2$, wherein said C$_1$-C$_8$-hydrocarbyl, aryl, arC$_1$-C$_8$ hydrocarbyl, heteroaryl, heteroarC$_1$-C$_8$-hydrocarbyl, cyclohydrocarbyl and heterocyclic groups in each of the R$^2$, R$^3$, R$^4$, R$^5$ and R$^6$ (R$^{2-6}$) substituents are themselves optionally substituted and wherein said optional substituents are selected from the group consisting of C$_1$-C$_8$-hydrocarbyl, aryl, arC$_1$-C$_8$-hydrocarbyl, heteroaryl, heteroarC$_1$-C$_8$-hydrocarbyl, heterocyclyl, cyclohydrocarbyloxy, heterocyclyloxy, —C(O)-aryl, hydrocarbyloxy, aryloxy, heteroaryloxy, —OC(O)—(C$_1$-C$_8$-hydrocarbyl), —OCH$_2$CH$_2$OH, —O(CH$_2$)$_3$CO$_2$H, 2-(morpholino)ethoxy, —(CH$_2$)$_k$OH (where k=1, 2 or 3), —CH$_2$NH$_2$, —CH$_2$NH(C$_1$-C$_8$-hydrocarbyl), —CH$_2$N(C$_1$-C$_8$-hydrocarbyl)$_2$, halogen, formyl, thioformyl, —CH=NOH, —CO$_2$H, thiocarboxyl, sulfonyl, C$_1$-C$_8$-hydrocarbyl-sulfonyl, arylsulfonyl, heteroarylsulfonyl, C$_1$-C$_8$-hydrocarbylsulfinyl, arylsulfinyl, heteroaryl-sulfinyl, —CO$_2$(C$_1$-C$_8$ hydrocarbyl, —C(O)NH$_2$, —C(O)NH(C$_1$-C$_8$-hydrocarbyl), —CON(C$_1$-C$_8$-hydrocarbyl)$_2$, —OH, —SH, —S—(C$_1$-C$_8$-hydrocarbyl), —S-aryl, —SO$_2$(C$_1$-C$_8$-hydrocarbyl), —SO$_2$N(C$_1$-C$_8$-hydrocarbyl)$_2$, C$_1$-C$_8$-hydrocarbylsulfonylamino, aryl sulfonylamino, —SO$_2$NH$_2$, —SO$_3$H, —SCF$_3$, —CN, —CHF$_2$, —CF$_3$, —NO$_2$, amino, —NH(C$_1$-C$_8$-hydrocarbyl, —N(C$_1$-C$_8$-hydrocarbyl)$_2$, arylamino, diarylamino, —NHSO$_2$(C$_1$-C$_8$hydrocarbyl), —C(O)NH(C$_1$-C$_8$-hydrocarbyl), and —C(O)N(C$_1$-C$_8$-hydrocarbyl)$_2$.

2. The method according to claim 1, wherein, one or more adjacent pairs of R$^2$, R$^3$, R$^4$, R$^5$ and R$^6$ together with the atoms to which they are bonded form an optionally substituted mono- or bicyclic aromatic ring or heteroaromatic ring Ar2 that is fused to depicted ring Ar1.

3. The method according to claim 1, wherein R* is $OR^1$, A is $OR^7$, and said boronic acid or borinic acid compound is a boronic acid compound.

4. The method according to claim 3, wherein the sulfenic acid of said biologically-active sulfenic acid-containing enzyme is present in an active site of the enzyme.

5. The method according to claim 3, wherein none of E, G, W, X or Y is N.

6. The method according to claim 5, wherein R* is $OR^1$, A is $OR^7$, each of $R^2$ and $R^4$ is hydrogen to provide a boronic acid compound of Formula V-1, below

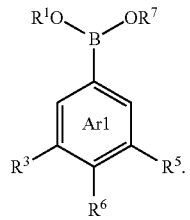

V-1

7. The method according to claim 6, wherein $R^7$ and $R^1$ are both H;

each of $R^3$, $R^5$, and $R^6$ is independently selected from the group consisting of nitro, halogen, $C_1$-$C_8$ hydrocarbyl, —$CHF_2$, —$CF_3$, $C_1$-$C_8$-hydrocarbyloxy, aryloxy and di-$C_1$-$C_8$-hydrocarbylamino.

8. The method according to claim 7, only one or none of $R^3$, $R^5$, and $R^6$ is other than hydrogen.

9. The method according to claim 1, wherein $R^2$, $R^3$, $R^4$, $R^5$ and $R^6$ are independently selected from the group consisting of hydrogen, 4-nitro, 3-nitro, 3-bromo, 4-bromo, 4-fluoro and 4-methoxy.

10. The method according to claim 1, wherein said biologically-active sulfenic acid-containing enzyme is selected from the group consisting of peroxiredoxin, protein tyrosine phosphatase, aldose reductase, Orp1, GAPDH, and nitrile hydratase.

* * * * *